(12) United States Patent
Calhoun et al.

(10) Patent No.: US 9,882,428 B2
(45) Date of Patent: Jan. 30, 2018

(54) ENERGY HARVESTING AND CONTROL FOR SENSOR NODE

(71) Applicants: UNIVERSITY OF VIRGINIA PATENT FOUNDATION, Charlottesville, VA (US); UNIVERSITY OF WASHINGTON THROUGH ITS CENTER FOR COMMERCIALIZATION, Seattle, WA (US)

(72) Inventors: Benton H. Calhoun, Charlottesville, VA (US); Brian Otis, Seattle, WA (US)

(73) Assignees: UNIVERSITY OF VIRGINIA PATENT FOUNDATION, Charlottesville, VA (US); UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 455 days.

(21) Appl. No.: 14/379,449

(22) PCT Filed: Feb. 15, 2013

(86) PCT No.: PCT/US2013/026390
§ 371 (c)(1),
(2) Date: Aug. 18, 2014

(87) PCT Pub. No.: WO2013/123359
PCT Pub. Date: Aug. 22, 2013

(65) Prior Publication Data
US 2015/0035378 A1    Feb. 5, 2015

Related U.S. Application Data

(60) Provisional application No. 61/600,467, filed on Feb. 17, 2012.

(51) Int. Cl.
*H02J 17/00*    (2006.01)
*A61B 5/04*    (2006.01)
(Continued)

(52) U.S. Cl.
CPC .......... *H02J 17/00* (2013.01); *A61B 5/04004* (2013.01); *A61N 1/3785* (2013.01);
(Continued)

(58) Field of Classification Search
CPC ........ A61B 5/04004; A61B 2560/0214; A61B 2560/0219; A61B 5/0402; A61B 5/0476;
(Continued)

(56) References Cited

U.S. PATENT DOCUMENTS 6,967,522 B2 * 11/2005 Chandrakasan ........ G05F 3/205
327/534
7,196,628 B2    3/2007 Hixson
(Continued)

FOREIGN PATENT DOCUMENTS

CN    101175981 A    5/2008
EP    2 283 881 A2    2/2011
(Continued)

OTHER PUBLICATIONS

Yanqing Zhang et al ; A Batteryless 19uW MICS/ISM-Band Energy Harvesting Body Sensor Node SoC for ExG Applications ; Jan. 2013; IEEE Journal of Solid-State Circuits, vol. 48, No. 1.*
(Continued)

*Primary Examiner* — Rexford Barnie
*Assistant Examiner* — Elim Ortiz
(74) *Attorney, Agent, or Firm* — Westerman, Hattori, Daniels & Adrian, LLP

(57) ABSTRACT

An integrated circuit, such as included as a portion of a sensor node, can include a regulator circuit having an input coupleable to an energy harvesting transducer. The inte-
(Continued)

grated circuit can include a wireless receiver circuit coupled to the regulator circuit and configured to wirelessly receive at least enough operating energy to establish operation of the sensor node without requiring the energy harvesting transducer. The integrated circuit can include a digital processor circuit coupled to the regulator circuit and a power management processor circuit. The digital processor circuit or one or more other circuits can include a subthreshold operational mode established by the power management processor circuit based on the selected energy consumption level. For example, establishing the subthreshold operational mode can include adjusting or selecting a supply voltage so as to establish subthreshold operation of a field effect transistor (FET) in the digital processor circuit or other circuits.

33 Claims, 15 Drawing Sheets

(51) Int. Cl.
<table>
<tr><td>A61N 1/378</td><td>(2006.01)</td></tr>
<tr><td>G06F 1/32</td><td>(2006.01)</td></tr>
<tr><td>A61B 5/0402</td><td>(2006.01)</td></tr>
<tr><td>A61B 5/0476</td><td>(2006.01)</td></tr>
<tr><td>A61B 5/0488</td><td>(2006.01)</td></tr>
<tr><td>G05F 1/613</td><td>(2006.01)</td></tr>
</table>

(52) U.S. Cl.
CPC ......... *A61N 1/3787* (2013.01); *G06F 1/3287* (2013.01); *A61B 5/0402* (2013.01); *A61B 5/0476* (2013.01); *A61B 5/0488* (2013.01); *A61B 2560/0214* (2013.01); *A61B 2560/0219* (2013.01); *G05F 1/613* (2013.01); *Y02B 60/1282* (2013.01)

(58) Field of Classification Search
CPC .. A61B 5/0488; A61N 1/3785; A61N 1/3787; G06F 1/3287; H02J 17/00; G05F 1/613; Y02B 60/1282
See application file for complete search history.

(56) References Cited

U.S. PATENT DOCUMENTS

<table>
<tr><td>7,205,177 B2</td><td>4/2007</td><td>De Raedt et al.</td></tr>
<tr><td>7,215,991 B2</td><td>5/2007</td><td>Besson et al.</td></tr>
<tr><td>7,466,240 B2</td><td>12/2008</td><td>Evans et al.</td></tr>
<tr><td>7,768,425 B2</td><td>8/2010</td><td>Evans et al.</td></tr>
<tr><td>7,933,642 B2</td><td>4/2011</td><td>Istvan et al.</td></tr>
<tr><td>2003/0078003 A1</td><td>4/2003</td><td>Hunter et al.</td></tr>
<tr><td>2007/0276270 A1*</td><td>11/2007</td><td>Tran ..................... A61B 5/0022 600/508</td></tr>
<tr><td>2008/0161660 A1*</td><td>7/2008</td><td>Arneson ............ A61B 1/00016 600/302</td></tr>
<tr><td>2008/0300660 A1*</td><td>12/2008</td><td>John .................... A61N 1/3785 607/61</td></tr>
<tr><td>2009/0076349 A1</td><td>3/2009</td><td>Libbus et al.</td></tr>
<tr><td>2009/0088608 A1</td><td>4/2009</td><td>Mumford et al.</td></tr>
<tr><td>2009/0303076 A1</td><td>12/2009</td><td>Setiadi et al.</td></tr>
<tr><td>2010/0039234 A1</td><td>2/2010</td><td>Soliven et al.</td></tr>
<tr><td>2010/0145236 A1</td><td>6/2010</td><td>Greenberg et al.</td></tr>
<tr><td>2010/0298720 A1</td><td>11/2010</td><td>Potkay</td></tr>
<tr><td>2011/0022025 A1</td><td>1/2011</td><td>Savoie et al.</td></tr>
<tr><td>2011/0066010 A1</td><td>3/2011</td><td>Moon et al.</td></tr>
<tr><td>2011/0106627 A1</td><td>5/2011</td><td>LeBoeuf et al.</td></tr>
<tr><td>2011/0245638 A1</td><td>10/2011</td><td>McKenna et al.</td></tr>
<tr><td>2012/0256492 A1</td><td>10/2012</td><td>Song et al.</td></tr>
</table>

FOREIGN PATENT DOCUMENTS

<table>
<tr><td>JP</td><td>2006-520132 A</td><td>8/2006</td></tr>
<tr><td>JP</td><td>2008-276297 A</td><td>11/2008</td></tr>
<tr><td>TW</td><td>200935769 A</td><td>8/2009</td></tr>
<tr><td>TW</td><td>M343203</td><td>10/2009</td></tr>
</table>

OTHER PUBLICATIONS

Extended European Search Report dated Oct. 21, 2015, issued in European Application No. 13749849.9 (8 pages).
Calhoun et al., "System Design Principles Combining Sub-threshold Circuits and Architectures with Energy Scavenging Mechanisms", IEEE, 2010, pp. 269-272.
Calhoun et al., "Modeling and Sizing for Minimum Energy Operation in Subthreshold Circuits", IEEE Journal of Solid-State Circuits, vol. 40, No. 9, Sep. 2005, pp. 1778-1786.
Chandrakasan et al., "Ultralow-Power Electronics for Biomedical Applications", Annual Review of Biomedical Engineering, Apr. 4, 2008, pp. 250-274.
Zhang et al., "A Batteryless 19 m MICS/ISM-Band Energy Harvesting Body Sensor Node SoC for ExG Applications", IEEE Journal of Solid-State Circuits, vol. 48, No. 1, Jan. 2013, pp. 199-213.
International Search Report dated Apr. 23, 2013 issued in corresponding application No. PCT/US2013/026390.
Kamath, "Designing Next-Generation Low Power Autonomous Sensor Nodes Using System-on-Chip Based Solutions", [online] URL=<http://rtpvisi.ece.virginia.edu/sites/default/files/Calhoun_ISCAS2010.pdf>, Dec. 2011, fig. 2 [online][retrieved on Apr. 2, 2013], Retrieved from the Internet<URL:http://www.cypress.com/?docID=32876>.
Office Action dated Sep. 5, 2016, issued in counterpart Chinese Patent Application No. 2013800201432, with English translation. (9 pages).
Office Action and Search Report dated Jul. 29, 2016, issued in counterpart Taiwanese Patent Application No. 102105665, with English translation. (14 pages).
E.J. Carlson, et al., "A 20 mV Input Boost Converter With Efficient Digital Control for Thermoelectric Energy Harvesting," J. Solid-State Circuits, vol. 45, No. 4, Apr. 2010.
D. Lake, et al., "Accurate Estimation of Entropy in Very Short Physiological Time Series: the Problem of Atrial Fibrillation Detection in Implanted Ventricular Devices," Am. J. Physiol Heart Circ Physiol, Jan. 2011.
S.C. Jocke, et al., "A 2.6-μW Sub-Threshold Mixed-Signal ECG SoC, " Dig. Symp. VLSI Circuits, Jun. 2009.
J. Pandey, et al., "A Sub-100uW MICS/ISM Band Transmitter Based on Injection-Locking and Frequency Multiplication,"J. Solid-State Circuits, vol. 46. No. 5, May 2011.
H. Kim, et al , "A Configurable and Low-Power Mixed Signal SoC for Portable ECG Monitoring Applications," Dig. Symp. VLSI Circuits, Jun. 2011.
S. Rai, et al., "A 500μW Neural Tag with 2μ Vrms AFE and Frequency-Multiplying MICS/ISM FSK Transmitter," ISSCC Dig. Tech. Papers, pp. 212-213, Feb. 2009.
N. Verma, et al., "A Micro-Power EEG Acquisition SoC with Integrated Feature Extraction Processor for a Chronic Seizure Detection System," J. Solid-State Circuits, vol. 45, No. 4, Apr. 2010.
L. Yan. et al., "A 3.9 mW 25-Electrode Reconfigured Sensor for Wearable Cardiac Monitoring System," J. Solid-State circuits, vol. 46, No. 1, Jan. 2011.
G. Chen, et al., "Millimeter-scale nearly perpetual sensor system with stacked battery and solar cells," ISSCC Dig. Tech. Papers, pp. 288-289, Feb. 2010.
B. Calhoun, et al., "System Design Principles Combining Sub-Threshold Circuits and Architectures with Energy Scavenging Mechanisms," Circuits and Systems (ISCAS), IEEE International Symposium, 2010.
Written Opinion of the International Searching Authority dated Apr. 23, 2013 issued in corresponding application No. PCT/US2013/026390.

(56) References Cited

OTHER PUBLICATIONS

Office Action dated Jan. 11, 2017 issued in corresponding Australian patent application No. 2013221336.
Office Action dated Jun. 6, 2017, issued in counterpart Chinese Application No. 201380020143.2, with English translation. (12 pages).
Office Action dated Sep. 27, 2017, issued in counterpart European Application No. 13 749 849.9 (5 pages).
Office Action dated Nov. 21, 2017, issued in counterpart Japanese Application No. 2017-114501, with English translation (6 pages).

* cited by examiner

ENERGY HARVESTING AND CONTROL FOR SENSOR NODE

CLAIM OF PRIORITY

Benefit of priority is hereby claimed to Calhoun et al., U.S. Provisional Patent Application Ser. No. 61/600,467, titled "Battery-less Energy Harvesting Sensor Node SoC and Related Method thereof," filed on Feb. 17, 2012, which is hereby incorporated by reference herein in its entirety, including its portions labeled "Appendix A" through "Appendix H."

BACKGROUND

Embedded systems can be used in a variety of applications, including providing monitoring, sensing, control, or security functions. Such embedded systems are generally tailored to specific applications, according to relatively severe constraints on size, power consumption, or environmental survivability.

In particular, one class of embedded system can include sensor nodes, such as for sensing or monitoring one or more physiologic parameters. A sensor node having wireless communication capability can be referred to as a Wireless Sensor Node (WSN). Similarly, a sensor node located on, nearby, or within a body of a subject can be referred to as a Body Area Sensor node (BASN) or Body Sensor node (BSN). Sensor nodes can provide significant benefit to care providers, such as enabling continuous monitoring, actuation, and logging of physiologic information, facilitating automated or remote follow-up, or providing one or more alerts in the presence of deteriorating physiologic status. The physiologic information obtained using the sensor node can be transferred to other systems, such as used to help diagnose, prevent, and respond to various illnesses such as diabetes, asthma, cardiac conditions, or other illnesses or conditions.

A sensor node can provide particular value to a subject or care giver if the sensor node includes certain features such as long-term monitoring capability or wearability, for example. A long lifetime for a sensor node without maintenance, replacement, or manual recharging becomes ever more important as health care costs escalate or as more care providers attempt to transition to remote patient follow-up and telemedicine. It is believed that generally-available sensor nodes are precluded from widespread adoption because of a lack of extended operational capability or wearability.

For example, sensor nodes including a large primary or rechargeable battery can be uncomfortable to wear, and a sensor node having a smaller battery is still undesirable because patients or other users may not comply with the required recharging or replacement interval. Similarly, sensor nodes requiring conductive data transfer interfaces are generally cumbersome, because the wearer or care giver must manually connect a communication interface cable to the node to transfer information to or from the node. Wireless communication circuitry may reduce or eliminate the need for such cumbersome wired interfaces. But, such wireless circuitry can consume substantial amounts of energy further taxing a limited energy budget or limiting operating life of generally-available sensor nodes.

Overview

A sensor node, such as a Body Sensor node (BSN), can include one or more semiconductor devices having a high degree of integration of various system functions. Such a semiconductor device can be referred to as a "System-on-a-Chip" or SoC. An SoC can provide digital or mixed signal circuitry realizing all major functions of the system, such as including one or more of general-purpose processor circuits, special purpose processor circuits, analog signal conditioning circuits, supply regulation or converter circuits, voltage or current reference circuits, or power management circuits.

The present inventors have recognized, among other things, that ultra-low power (ULP) techniques can be applied to one or more circuits included in a sensor node. ULP techniques can be used to realize an SoC included as a portion of a sensor node. For example, such an SoC for a sensor node can include one or more analog or digital portions configured for subthreshold operation.

Other techniques can be used instead of subthreshold operation, or in addition to sub-threshold operation, such as power or clock gating to disable or suspend operation of specified sections of the system, or including adjusting a duty cycle, a clock frequency (e.g., clock throttling), or a supply parameter (e.g., supply voltage throttling) so as to reduce power consumption.

The present inventors have also recognized that an operable lifetime of a sensor node can be substantially increased using energy harvesting from ambient energy sources. For example, such energy can be obtained using a thermal gradient or a mechanical vibration. Energy harvesting techniques can provide an extended operable lifetime as compared to sensor nodes reliant upon a battery. However, to provide sustained operation, an energy-harvesting sensor node generally must consume less energy than the amount harvested.

To that end, the present inventors have also recognized that a power management processor circuit can be used to enable, disable, throttle, or re-route data through various system sections, such as in response to monitored conditions, in a closed-loop manner. For example, the amount of energy provided by an energy harvesting transducer can vary over time. The power management processor circuit can monitor information indicative of the level of energy provided by the energy harvesting transducer. Using the monitored information, the power management circuit can adjust the energy consumption level of the sensor node to provide continued (e.g., sustained) operation of the sensor node in the face of varying input energy.

Energy consumption can be specified in terms of modes or levels, such as using a three or four level energy consumption scheme, or other scheme. The sensor node can toggle between such energy consumption levels to avoid extinction or reset. In the event of a reset, the sensor node can statefully recover to a specified mode of operation, such as resuming monitoring, communication, or one or more other functions.

In an example, a sensor node can be battery-less, such as operable without requiring a primary or rechargeable battery on-board or within the sensor assembly. In one approach, a boost converter circuit and regulator configuration can be used that can covert a relatively low-voltage output of a thermoelectric generator (TEG), such as in the tens of millivolts (mV), to a higher voltage level specified for use with one or more other sections of sensor node circuitry. In an example, a wireless receiver circuit can be coupled to one or more of the boost circuit or regulator, such as to receive an initial burst of wirelessly-coupled energy to establish operation of the sensor node.

In an example, an integrated circuit, such as included as a portion of a sensor node, can include a regulator circuit having an input coupleable to an energy harvesting transducer. The integrated circuit can include a wireless receiver circuit coupled to the regulator circuit and configured to wirelessly receive sufficient operating energy to establish operation of the sensor node without requiring the energy harvesting transducer. The integrated circuit can include a digital processor circuit coupled to the regulator circuit and a power management processor circuit. The digital processor circuit or one or more other circuits can include a subthreshold operational mode established by the power management processor circuit based on the selected energy consumption level. For example, establishing the subthreshold operational mode can include adjusting or selecting a supply voltage so as to establish subthreshold operation of a field effect transistor (FET) in the digital processor circuit or other circuits.

Applications of sensor nodes described in the examples herein need not be restricted to biological or health-monitoring applications. For example, such sensor nodes can be used in a variety of applications more generally related to remote monitoring or remote sensing, such as supporting supervisory control or automation of utility, infrastructure, or energy systems, structural health monitoring, surveillance, or environmental monitoring such as habitat monitoring or wildlife management.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
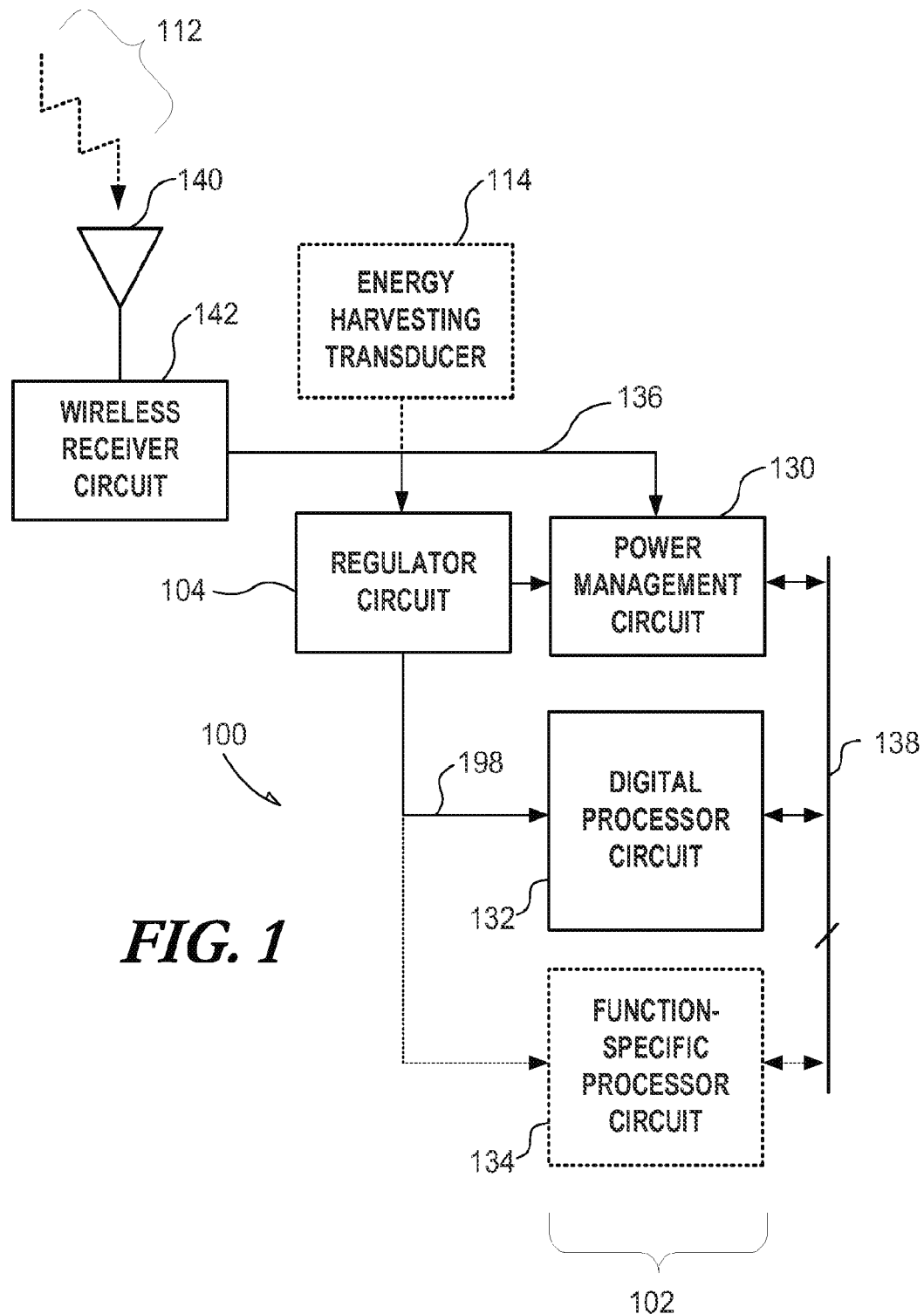
FIG. 1 illustrates generally an example of a system that can include a regulator circuit, a power management circuit, a wireless receiver circuit, or a digital processor circuit.

FIG. 1 illustrates generally an example of a system 100, such as a sensor node. The system 100 can include a regulator circuit 104, a power management processor circuit 130, a wireless receiver circuit 142, or a digital processor circuit 132. The system 100 can include an antenna 140 configured to receive electromagnetically-coupled energy 112, such as using radiative coupling or inductive coupling, for example. Such electromagnetically-coupled energy 112 can be referred to as radio-frequency (RF) energy, such as corresponding to a specified range of frequencies selected from about the kilohertz (kHz) range to the tens or hundreds of megahertz (MHz) range, or including one or more other ranges of frequencies. The wireless receiver circuit 142 can include a tuned receiver, pre-selector, or one or more other circuits, such as to capture electromagnetically-coupled energy 112 corresponding to the specified range of frequencies or to reject other ranges of frequencies.

The system 100 can include or can be coupleable to an energy harvesting transducer 114, such as one or more of a piezoelectric transducer, a mechanical-to-electric transducer such as a linear or rotary device, a photo-voltaic transducer or other optical-to-electrical transducer, or a thermoelectric generator (TEG), for example. An input 136 to a regulator circuit 104 can be driven by energy received from one or more of the wireless receiver circuit 142, or the energy harvesting transducer 114. In this manner, the system 100 can receive operating energy using the wireless receiver circuit 142 or the energy harvesting transducer 114. For example, the system 100 can be battery-less or can operate without requiring a primary or rechargeable battery, such as powered continuously or for an extended period of operating using one or more of wirelessly-coupled energy 112 or energy provided by the energy harvesting transducer 114.

The regulator circuit 104 can provide one or more outputs, such as one or more fixed or adjustable output voltages, to one or more other portions of the system 100, such as including a supply node 198. As shown in examples below, the energy obtained from the energy harvesting transducer 114 may be conditioned or converted by one or more other circuits, such as a voltage boosting converter.

The input to the regulator circuit 104 can be coupled to the power management processor circuit 130, such as monitored by the power management processor circuit 130. The power management processor circuit 130 can be coupled to other sections of the system 100, such as using one or more buses (e.g., a first bus 138) coupled to one or more of the digital processor circuit 132, or other functional blocks such as a function-specific processor circuit 134.

One or more portions of a digital section 102 of the system 100 can include a subthreshold operational mode. A subthreshold operational mode can be established such as providing, adjusting, or selecting a supply voltage provided by the regulator circuit so as to establish subthreshold operation of a field effect transistor (FET) in one or more of the power management processor circuit 130, the digital processor circuit 132, the function-specific processor circuit 134, or in one or more other circuits of the system 100, such as in one or more digital or mixed signal circuits.

Subthreshold operation can be described as operating one or more FETs in a weak-inversion mode where a gate-to-source voltage is established at or below a threshold voltage ($V_t$) for the one or more FETs, resulting in a primarily exponential dependence on drain-to-source current as a function of gate-to-source voltage. Various techniques can be used to establish subthreshold operation, such as providing a supply voltage having a VDD-to-VSS voltage below the threshold voltage of all FETs in a section coupled to the supply voltage.

A tradeoff can exist between energy efficiency, maximum clock speed, and supply voltage. Subthreshold operation need not be restricted to a single supply voltage. For example, one or more of a clock frequency or a supply voltage can be adjusted such as to provide a specified level of computational capability or other operational performance while maintaining low power consumption, as discussed in the examples below.

Other criteria can be used to specify or describe subthreshold operation, such as using a current density perspective. For example, subthreshold operation can be described as a region of FET operation where transconductance (e.g., $g_m$) is at a relative or absolute maximum, or where transconductance is primarily dependent on threshold voltage and drain current, and exhibits only a weak (or no) dependence on variation in gate-to-source voltage. Such subthreshold operation, along with or instead of other techniques, can provide the system 100 with extended longevity even though the available energy obtained using the wireless receiver circuit or energy harvesting transducer may be quite limited (e.g., on the order of microwatts).

The power management processor circuit 130 can be configured to adjust an energy consumption level of the system 100, such as using information obtained by monitoring the input 136 to the regulator circuit 104, or by monitoring other system parameters such as other voltages, currents, or operating states.

Figure 2:
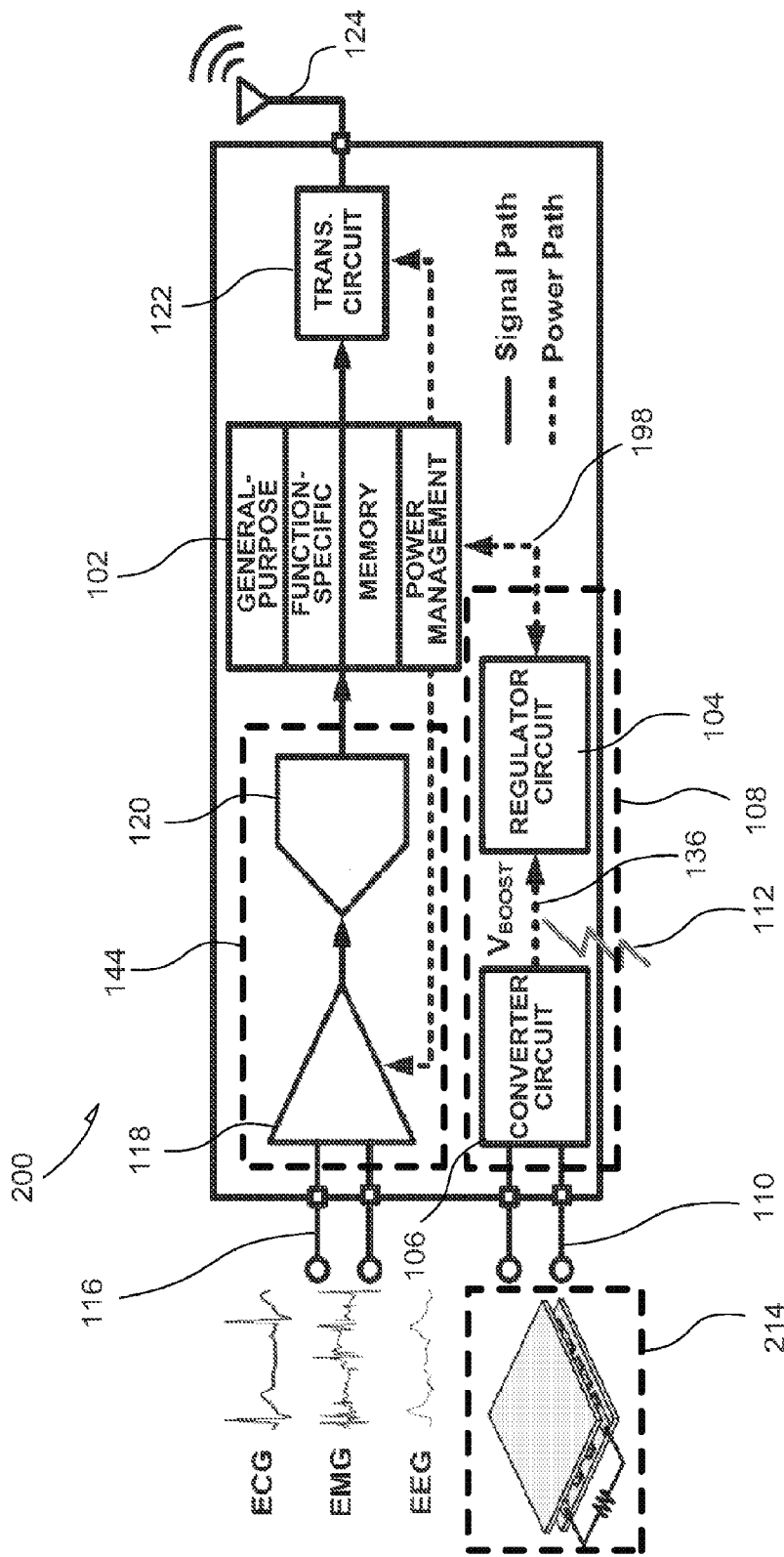
FIG. 2 illustrates generally an example of a system that can include an analog input configured to obtain information indicative of one or more physiologic signals.

FIG. 2 illustrates generally an example of a system 200, such as similar to or incorporating aspects of the example of FIG. 1. The system 200 can include an analog input 144 configured to obtain information indicative of one or more physiologic signals such as an electrocardiogram (ECG), an electroencephalogram (EEG), or an electromyogram (EMG), for example. Such physiologic signals can be referred to generically as "ExG" signals. Other physiologic information can be obtained, such as corresponding to one or more other physiologic parameters such as respiration, neural activity, or motion, for example. The analog input 144 need not be restricted to obtaining physiologic information. For example, other information can be obtained by the analog input such as for applications including remote monitoring, sensing, surveillance, or for other applications.

In the example of FIG. 2, the analog input 144 (or "analog front end" (AFE)) can include one or more amplifier stages to buffer or amplify a physiologic signal coupled to an input node 116. An output of an amplifier 118 can be coupled to an analog-to-digital converter 120, such as a converter 120 including a successive approximation register (SAR) topology.

The system 200 can include a digital section 102, such as including a general-purpose processor circuit (e.g., a microcontroller unit or other general-purpose processor circuit), one or more function-specific processor circuits (e.g., an "accelerator" circuit geared to performed one or more functions), one or more memory circuits, or a power management processor circuit. The system 200 can include a wireless transmitter circuit 122, such as for telemetering information from the system 200 to other systems or locations.

Figure 3:
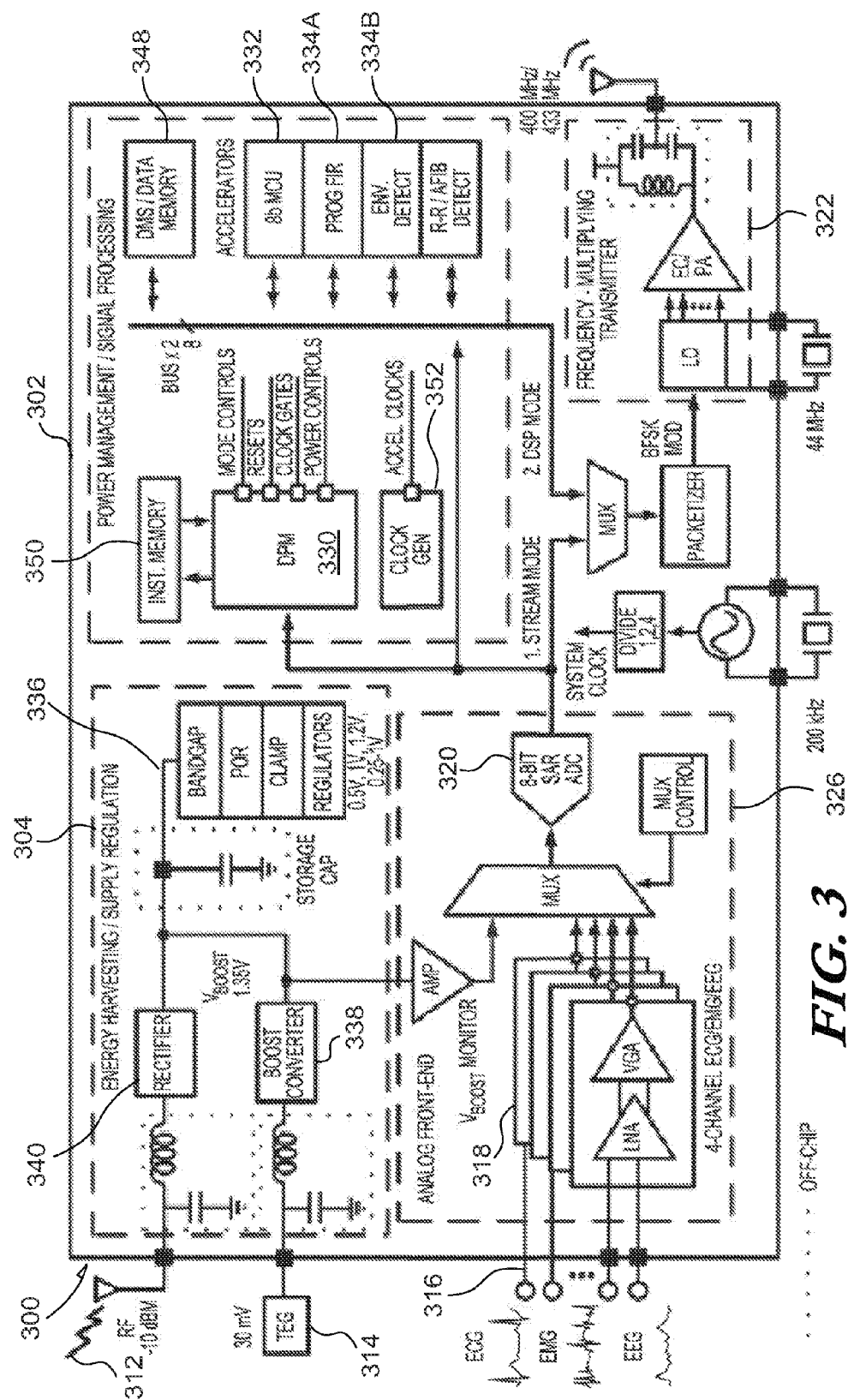
FIG. 3 illustrates generally an illustrative example of a system that can include an analog input, a power management circuit, a regulator circuit block, one or more function-specific processor circuits, or a general-purpose processor circuit.
Figure 4A:
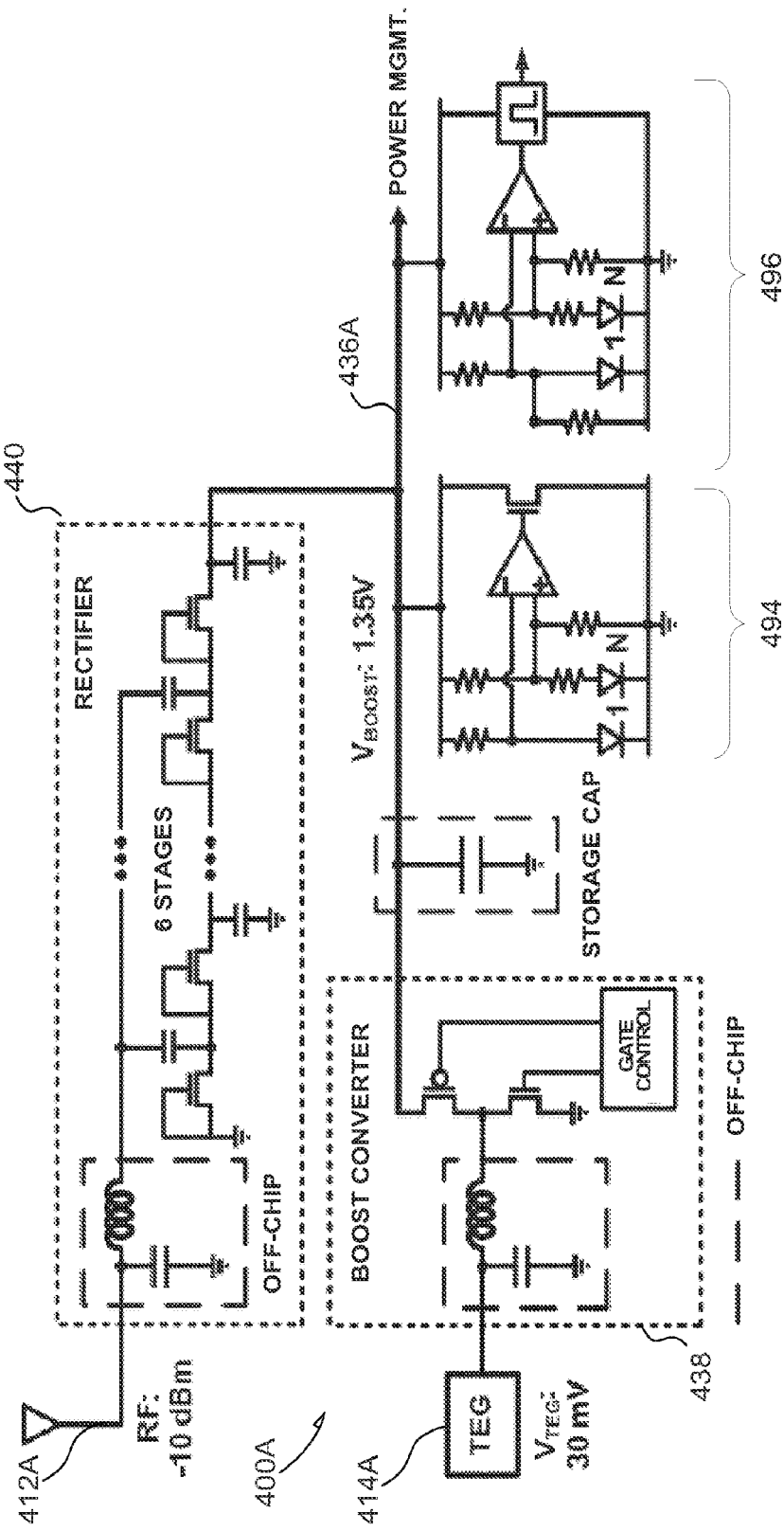
FIG. 4A illustrates generally an illustrative example of a portion of a system that can include a wireless receiver circuit or a converter circuit.

As discussed in the example of FIG. 1, and elsewhere, the system 200 can include a regulator section 108 such as including a converter circuit 106 coupled to one or more regulator circuits, such as a regulator circuit 104. The output 198 of the regulator circuit 104 can be coupled to other sections of the system 200. The regulator section 108 can include a wireless receiver, such as configured to receive electromagnetically-coupled operating energy 112. For example, a TEG 214 or other energy harvesting transducer can be coupled to an input 110 of a converter circuit, and the converter circuit can provide an output, such as coupled to the regulator circuit 104, such as shown in the examples of FIG. 3 or FIG. 4A. The output of the converter circuit 106 can be insufficient to establish initial operation of the system 200. For example, the energy provided by the TEG 214, such as obtained from body heat of a subject, may be sufficient to sustain continued operation of the system 200. However, such energy may be insufficient to start or establish initial operation of the system 200.

Figure 4B:
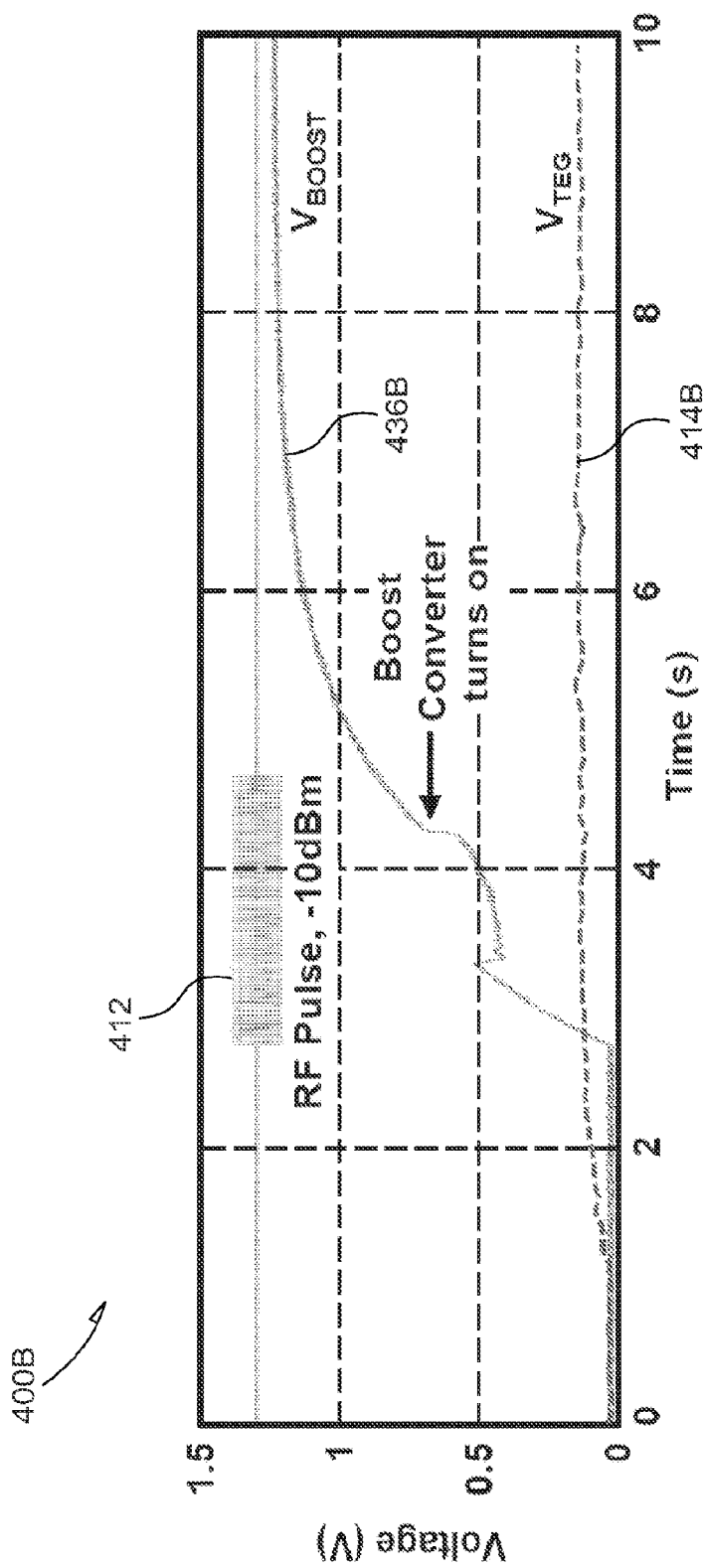
FIG. 4B illustrates generally an illustrative example of plots corresponding to a wirelessly-coupled burst pulse provided to a wireless receiver circuit, an output node of a power converter circuit, and an input to the power converter circuit corresponding to an output of an energy harvesting transducer, such as can be obtained experimentally using at least a portion of a system as shown in the examples of FIG. 3 or 4B.

In this scenario, electromagnetically-coupled energy 112 can be received by the regulator section 108 such as to establish sufficient energy at the converter circuit 106 output to "kick start" one or more regulation or control functions of the system 200, or to establish an initial charge state on one or more capacitors included in the system, as shown in the illustrative example of FIG. 4B.

FIG. 3 illustrates generally an illustrative example of a system 300, such as similar to or incorporating aspects of the examples of one or more of FIG. 1 or 2. The system 300 can include a regulator section 304, an analog input 326 (e.g., an analog front end), a digital section 302 (e.g., including one or more portions configured for subthreshold operation), a wireless transmitter 322, or one or more other functional blocks or sections.

Figure 12:
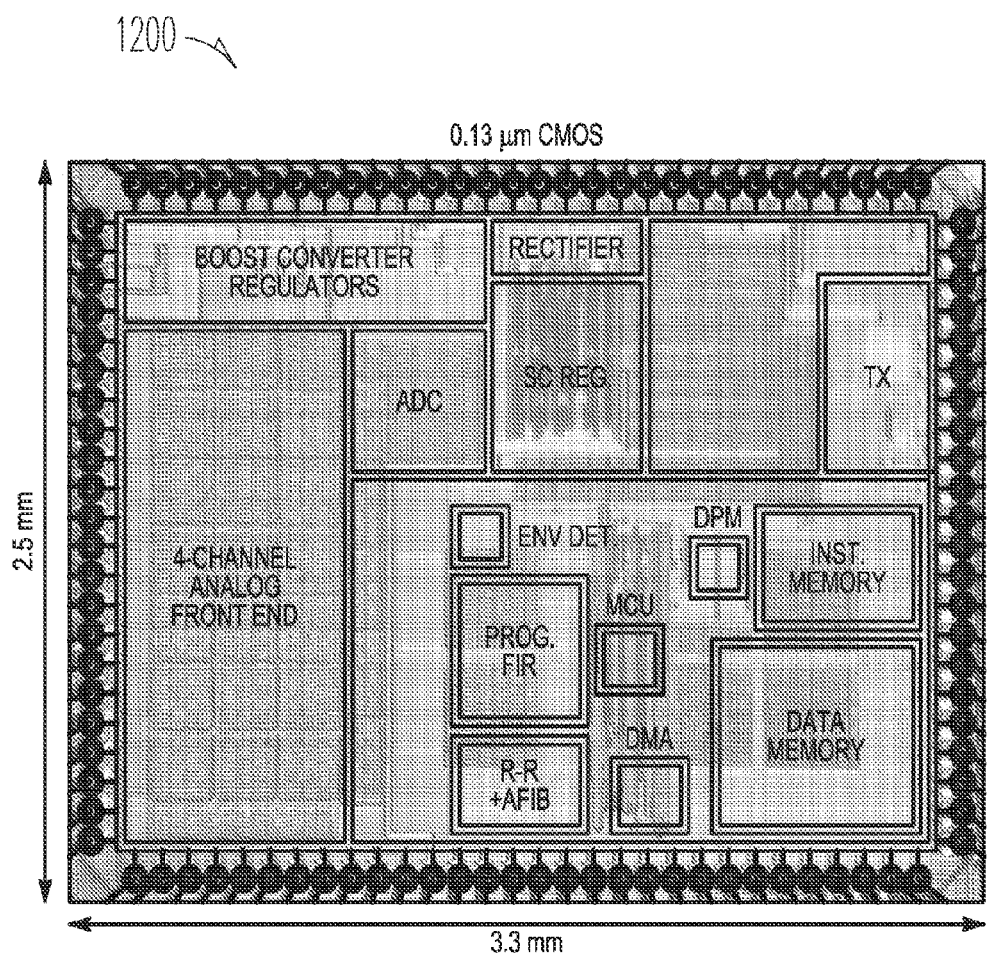
FIG. 12 illustrates generally an annotated micrograph of an integrated circuit, such as corresponding to at least a portion of the system of the illustrative example of FIG. 3.

One or more portions of the system 300 can be co-integrated as a portion of a commonly-shared integrated circuit, such as a complementary metal-oxide-semiconductor (CMOS) integrated circuit, such as shown in the illustrative example of FIG. 12. Use of the phrase "metal-oxide-semiconductor" does not imply that a gate electrode must be metallic. A gate electrode in a FET included in a CMOS circuit may include a polysilicon conductive portion, or other conductive portion.

Figure 8:
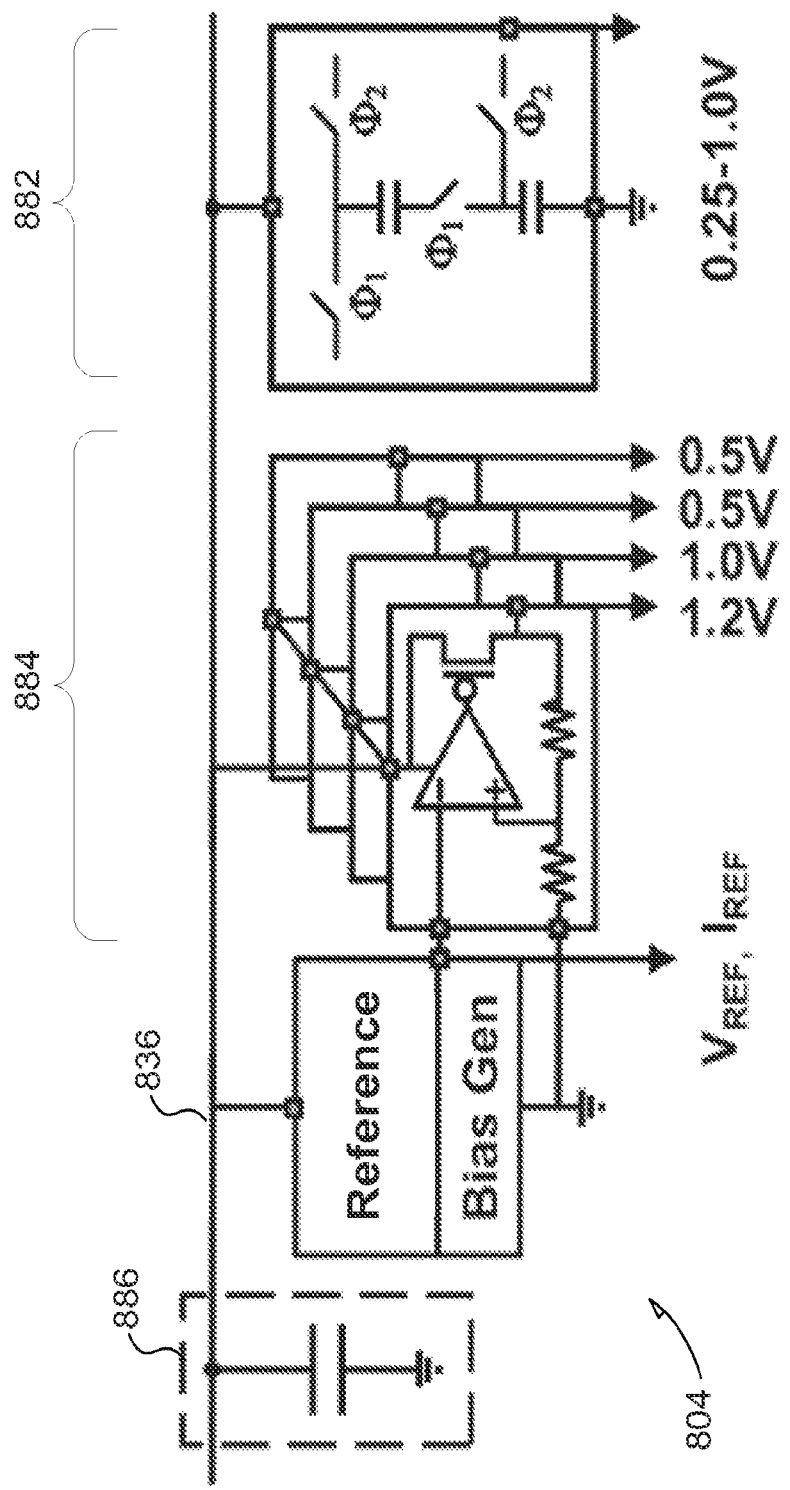
FIG. 8 illustrates generally an illustrative example of a portion of a system, such as a portion of a regulator circuit that can be included as a portion of a sensor node.

In the illustrative example of FIG. 3, the regulator section 304 can include various circuits or subsystems, such as shown in the illustrative examples of FIG. 4A or 8. The regulator section 304 can be coupled to a TEG 314. The regulator section 304 can include a boost converter 338, such as configured to convert energy from the TEG from a voltage level of about 30 mV up to specified boosted voltage, such as about 1.35V, at a boost converter 338 output node 336 (e.g., $V_{BOOST}$), such as coupled to a storage capacitor (e.g., an off-chip storage capacitor).

In the illustrative example of FIG. 3, the regulator section 304 can include multiple regulator circuits, such as to provide respective regulated voltage supplies to other portions of the system 300. For example, the regulator section 304 can include other circuits, such as one or more reference circuits (e.g., a bandgap reference), or one or more clamp circuits. Electromagnetically-coupled energy 312 can be provided to the boost converter 338 output node 336, such as using a rectifier circuit 340. The regulator section can use a clamp circuit to prevent an overvoltage condition output node 336 of the boost converter 338.

Figure 9:
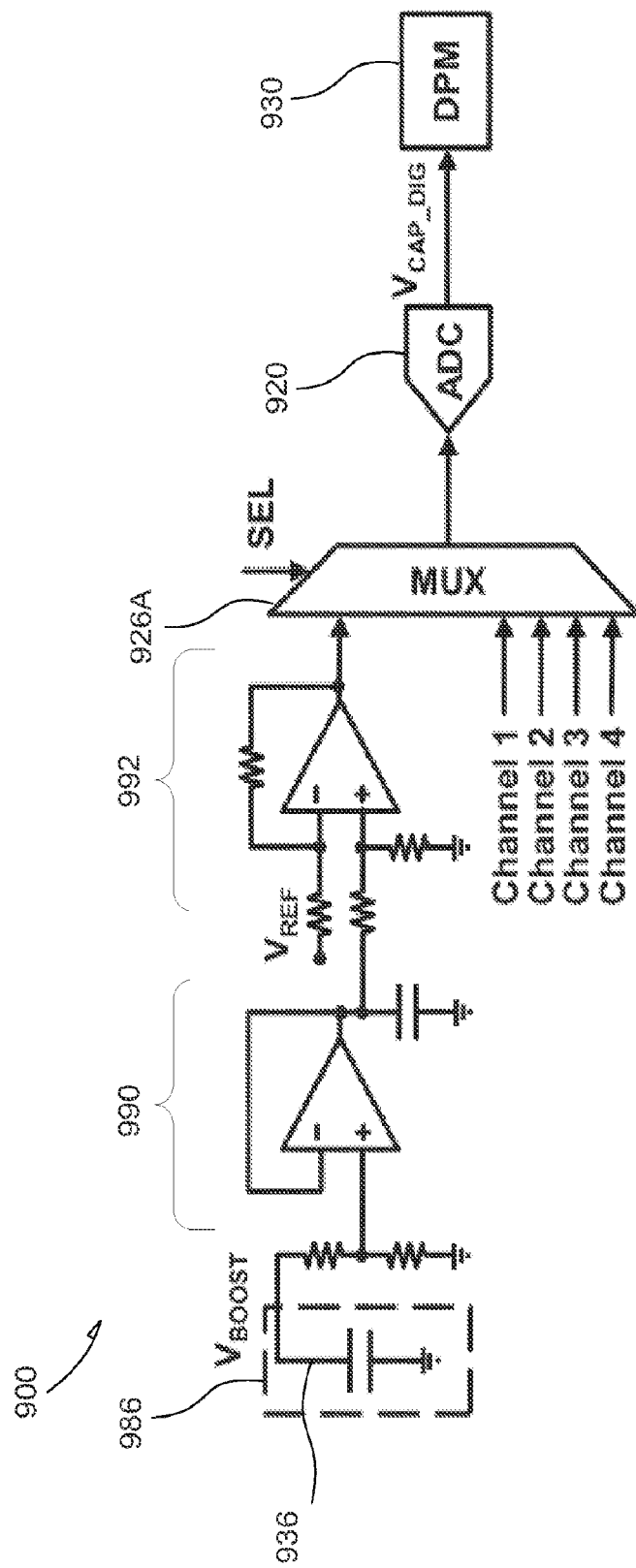
FIG. 9 illustrates generally an illustrative example of a portion of a system that can include a monitoring circuit configured to provide information indicative of a regulator circuit input.

The analog input 326 can include respective input channels 318, such as a four-channel configuration shown in the illustrative example of FIG. 3 or 9. Respective input channels can include respective low noise amplifiers (LNAs), such as coupled to respective fixed or variable gain amplifiers (VGAs). One or more analog-to-digital converters can be included, such as an 8-bit SAR ADC 320 as shown in the illustrative example of FIG. 3. The respective input channels 318 can be multiplexed to the ADC 320, such as using a multiplexer. The use of a cascaded LNA and VGA configuration can provide scaling of a physiologic signal in the range of a few microvolts (μV) to approach a full range of the ADC 320. Such scaling can be used to relax a vertical bit-resolution of the ADC while still preserving sufficient resolution for acquisition or analysis of physiologic signals, such as consuming less than about 4 microwatts (μW) per channel.

Information obtained using the analog input 326 can be provided to the digital section 302. The digital section 302 can be configured for subthreshold operation, such as under the control of a digital power management (DPM) processor circuit 330. The DPM 330 can provide mode control for the system 300, such as to control an energy consumption state of the system 300 according to specified energy consumption levels. Such energy consumption control can include power or clock throttling or gating to various other sections.

For example, energy consumption, such as using the DPM 330, can be controlled by selecting or adjusting one or more voltage supplies provided by the regulator section 304, such as to automatically adjust the voltage provided to one or more other functional blocks (e.g., providing "dynamic voltage scaling" (DVS)), such as based on monitoring the output node 336 of the boost converter or otherwise estimating available energy.

The digital section 302 can include other circuits, such as a general-purpose processor circuit 332 (e.g., a microprocessor or an 8-bit microcontroller unit (MCU)). The digital section 302 may include one or more function-specific processor circuits (e.g., function-specific "accelerators"), such as can include a programmable filter 334A (e.g., a finite impulse response (FIR) filter), an envelope detection circuit 334B, or other function-specific circuits (e.g., a fibrillation detection circuit, an R-wave-to-R-wave interval estimator circuit). The digital section 302 can include one or more memory circuits, such as an instruction memory circuit 350 (e.g., a including 1.5 kiloBytes in the illustrative example of FIG. 3). The instruction memory circuit 350 can be implemented as a read-only memory (ROM), or can be a reprogrammable random-access memory (RAM), such as a static RAM (SRAM) circuit.

In the illustrative example of FIG. 3, the system 300 can include a modified Harvard architecture, such as including a data memory circuit 348, such as separate from the instruction memory circuit 350. Other memories or buffers can be included, such as a first-in-first-out (FIFO) buffer topology.

Figure 6:
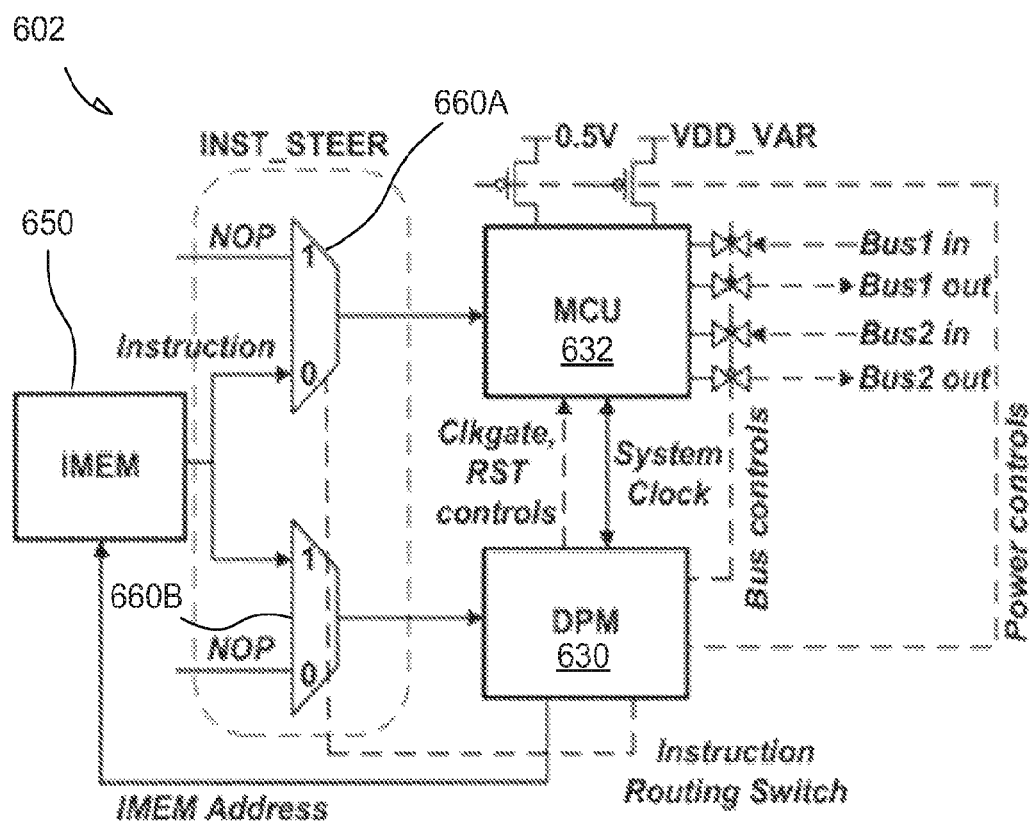
FIG. 6 illustrates generally an illustrative example of a portion of a system that can include an instruction memory that can be shared between a general-purpose processor circuit, a power management circuit, or one or more other circuits such as a function-specific processor circuit.

As shown in the illustrative example of FIG. 6, the DPM 330 can include a simplified instruction set architecture (ISA), such as configured to operate according to instructions stored in the instruction memory circuit 350. Similarly, the general-purpose processor circuit 332 can also be configured to operate according to instructions stored in the instruction memory circuit 350. However, the general-purpose processor circuit 332 need not use the same instruction set as the DPM 330.

In an illustrative example, one or more portions of the system 300 can include an N-strong CMOS integrated circuit technology, such as including one or more memory circuits (e.g., SRAMs). For example, one or more memory circuits of the system 300 can include an 8-transistor bitcell topology, such as similar to a topology shown in Verma et al., "A 256 kb 65 nm 8T Subthreshold SRAM Employing Sense-Amplifier Redundancy," IEEE Journal of Solid-State Circuits, vol. 43, issue 1, pp. 141-149, January 2008, which is incorporated herein by reference in its entirety. In an illustrative example, such as to eliminate half-select instability during a write, both reads and writes can be applied to full rows of memory.

In an illustrative example, the data memory circuit 348 can be partitioned into banks, such as 4×1 kB banks that can be individually power gated by NMOS footers overdriven to 1.2V when active to enhance ground reference stability. Such power gating can be controlled by the DPM 330, such as corresponding to a specified energy consumption level of the system 300.

In such an illustrative example, experimentally-obtained measurements can indicate reliable operation of such a memory topology, such as implemented at a 130 nanometer (nm) processor node, to an 0.3V supply voltage, such as clocked at about 200 kHz.

As shown in the illustrative example of FIG. 3, the system 300 can include a wireless transmitter circuit 322. For example, such a transmitter circuit can be configured to operate in a Medical Implant Communications Service (MICS) band, such as within a range of frequencies above about 400 MHz to about 433 MHz, or using an Industrial-Scientific-Medical (ISM) band, or using one or more other ranges of frequencies allocated by a relevant spectrum allocation authority for use in the sensor node application.

In the illustrative example of FIG. 3, information obtained using the ADC 320 can be coupled to a packetizer and streamed by the transmitter circuit 322, such as without requiring processing by the digital section 302, or such information can be provided by the digital section 302, such as during or after processing. For example, such information can include a digitized representation of a physiologic signal or other sensed signal, or such information can include one or more parameters extracted from such signals, such as shown in illustrative examples of FIG. 11A or 11B.

The wireless transmitter circuit 322 can be configured for sub-milliwatt (mW) operation, such as duty-cycled or otherwise enabled or disabled under the control of the DPM 330, avoiding a need for one or more large discrete bucket or filtering capacitors. The wireless transmitter circuit 322 can use frequency-shift-keying (FSK) modulation, such as binary FSK (BFSK), such as to provide about a 200 kilobit-per-second (kbps) transmission rate, or one or more other modulation techniques, operating frequency ranges, or data rates.

In an illustrative example, the wireless transmitter circuit 322 can include a frequency-multiplying transmitter architecture to reduce synthesizer power by operating a local oscillator (LO) at about 1/9 of a specified carrier frequency. For example, equally spaced edges can be generated using cascaded ring oscillators to drive an edge-combiner (EC) embedded power amplifier (PA) to perform such frequency multiplication. In this manner, such frequency multiplication can provide harmonic injection-locking from a crystal oscillator. Such a technique need not use a phase-locked loop (PLL), instead injection-locking a low-frequency ring oscillator to an on-chip crystal reference. Such injection locking can provide rapid settling time, as compared to a PLL-based approach, such as allowing aggressive duty-cycling of the wireless transmitter circuit 322.

Directly injection-locking a multi-phase ring oscillator using a single-phase reference can induce significant mismatch. Instead, a cascaded multi-phase injection-locking scheme can be used to correct the phase and amplitude mismatches. On-chip BFSK modulation can be provided by pulling a quartz reference clock. For example, by modulating a load capacitor, the crystal frequency can be pulled by about 200 parts-per-million (ppm). In this illustrative example, after 9× multiplication, the wireless transmitter circuit can be provide a frequency deviation of about 100 kHz, and can provide greater than about a 100 kbps wireless information transfer rate.

In an illustrative example, the wireless transmitter circuit 322 can consume about 160 µW when transmitting at a transfer rate of about 200 kbps. As shown in the illustrative examples of FIGS. 11A and 11B, in streaming data transfer mode, the wireless transmitter circuit 322 can operate at a 100% duty-cycle. In another mode (such as corresponding to a different energy consumption level), such as an R-wave-to-R-wave extraction mode, the wireless transmitter circuit 322 can be duty-cycled. Such duty-cycling can reduce the wireless transmitter circuit 322 power consumption to about 0.013%, corresponding to about 190 nW of power dissipation. A packetizer can be configured to provide a programmable or specified packet header and cyclic-redundancy-check (or other error detection or error correction), such as to provide compatibility with generally-available receiver circuits.

FIG. 4A illustrates generally an illustrative example 400 of a portion of a system, such as a sensor node, that can include a wireless receiver circuit 440 (e.g., a rectifying circuit), or a converter circuit 438 (e.g., a boost converter).

The converter circuit 438 can be coupled or coupleable to a TEG 414A. The converter circuit 438 can provide an output 436A (e.g., $V_{BOOST}$) coupled to other portions of a system such as a sensor node, such as shown in the examples of FIGS. 1 through 3 or elsewhere. For example, a reset generation circuit 496 can be coupled to the output 436A, such as to generate or inhibit a power-on reset (POR) in response to monitoring a voltage provided at the output 436A.

TEGs are generally constructed of thermopiles in series, such as configured to provide a voltage established from a specified temperature difference across the TEG 414A, for a specified size (e.g., area). For example, a Seebeck coefficient of a generally-available thermocouple (e.g., bismuth telluride) can be about ±0.2 millivolts (mV) per degree Celsius (mV/° C.).

For a specified temperature gradient of about 1° C., a 1×1 centimeter (cm) TEG can generally provide much less than 1V. Such a temperature gradient can be further reduced by the environment nearby the TEG 414A. For example, air surrounding a TEG 414A can present a large thermal resistance that can dramatically reduce an effective temperature gradient across the thermopiles, further limiting the voltage available at the TEG 414A output. Accordingly, a system using an energy harvesting transducer such as the TEG 414A can be configured to boost a TEG output, which may only be in the range of tens of mV, to a higher voltage level. Various converter circuit 438 topologies can be used, such as a converter architecture shown in Carlson et al., "A 20 mV Input Boost Converter With Efficient Digital Control for Thermoelectric Energy Harvesting," IEEE Journal of Solid-State Circuits, vol. 45, no. 4, April 2010, which is herein incorporated by reference in its entirety.

In an illustrative example that can include a TEG 414A, one or more other sources of operating energy can be used to assist in establishing initial operation (e.g., start-up) of the system (e.g., a sensor node). Such other sources of operating energy can include batteries or mechanical switches. However, such batteries or switches can be bulky. The present inventors have recognized, among other things, that wirelessly-coupled energy (e.g., a radio-frequency (RF) pulse) can be provided to the antenna 412A of the wireless receiver circuit 440, such as used to establish initial operation of the system. For example, incident electromagnetically-coupled operating energy, such as at a relatively low power level of −10 decibels relative to 1 mw (dBm) can be provided, such as for 1-2 seconds, to pre-charge one or more storage capacitors, or to establish specified initial conditions at one or more nodes of the system.

In the example 400 of FIG. 4A, electromagnetically-coupled energy (e.g., radiatively or inductively coupled) can be rectified by the receiver circuit 440. The example 400 can include other circuits, such as a shunt clamp circuit 494, such as to constrain the output node 436A to a specified range of voltages in order to prevent a potentially damaging over-voltage condition in the presence of received electromagnetically-coupled operating energy. One or more portions of the example of FIG. 400 can be co-integrated on a commonly-shared integrated circuit. Larger passive components, such as one or more inductors or capacitors, can be located on a commonly-shared printed circuit assembly or module, and coupled to the integrated circuit. Such components can be referred to "off-chip."

As discussed above, incident electromagnetically-coupled operating energy can be provided, such as at a level of about −10 dBm at an input to the receiver circuit. A 6-stage rectifying charge pump circuit can be used to couple the incident electromagnetically-coupled operating energy to the output node 436A. The reset generation circuit 496 can be bandgap-referenced, and can provide a POR to the system, such as by monitoring the output node 436A. For example, when the output node, $V_{BOOST}$, reaches about 1V, a POR can be de-asserted.

Hysteresis in the reset generation circuit 496 can prevent unwanted toggling of the POR circuit. For example, a POR trigger level can be specified so as to allow a POR to be generated when the output node 436A drops below a specified voltage where the chip fails to function correctly, which may be well below 1V. Such a specified trigger voltage, $V_{KILL}$, can be determined using information about the minimum $V_{BOOST}$ voltage that results in correctly-generated reference voltages or sustained energy conversion reliability.

FIG. 4B illustrates generally an illustrative example of plots corresponding to a wirelessly-coupled burst pulse 412 provided to the wireless receiver circuit 440 of FIG. 4A, a plot of a voltage 436B of an output node 436A of the power converter circuit 438 of FIG. 4A, and a plot 414B of an input to the power converter circuit 438, corresponding to an output of an energy harvesting transducer, such as can be obtained experimentally using at least a portion of a system as shown in the examples of FIG. 3 or 4B.

The TEG plot 414B illustrates generally that an initial ramp up and stabilization of the voltage that can be provided by the TEG. For example, as shown in FIG. 4B, after the TEG output settles, a short burst pulse 412 can be provided to wireless charge a storage capacitor on the output node 436A as shown in the plot 436B. In this illustrative example, shortly after the voltage on the output node 436A reaches 600 mV, the boost converter can function and can further charge the storage capacitor to about 1.35V. The system can then continue to function without further burst pulses 412, such as for an extended period of time or continuously. However, if the output node (e.g., $V_{BOOST}$), drops below a specified trigger voltage (e.g., $V_{KILL}$), such as due to a prolonged period of consumption exceeding harvested energy or in the absence of harvested energy, the system can reset, or operation can be entirely extinguished. Such extinction can be referred to as "node death."

In an example where the output node 436A dips below a trigger voltage, such as $V_{KILL}$, the system can automatically shut down. The system can then be "revived" or restarted, such as using a sequence as shown in the illustrative example of FIG. 4B. The system may statefully restart, such as using a non-volatile memory including a program state stored before shutdown, or the system can re-start from a specified memory location including a boot loader or default program, such as included in ROM.

Figure 5:
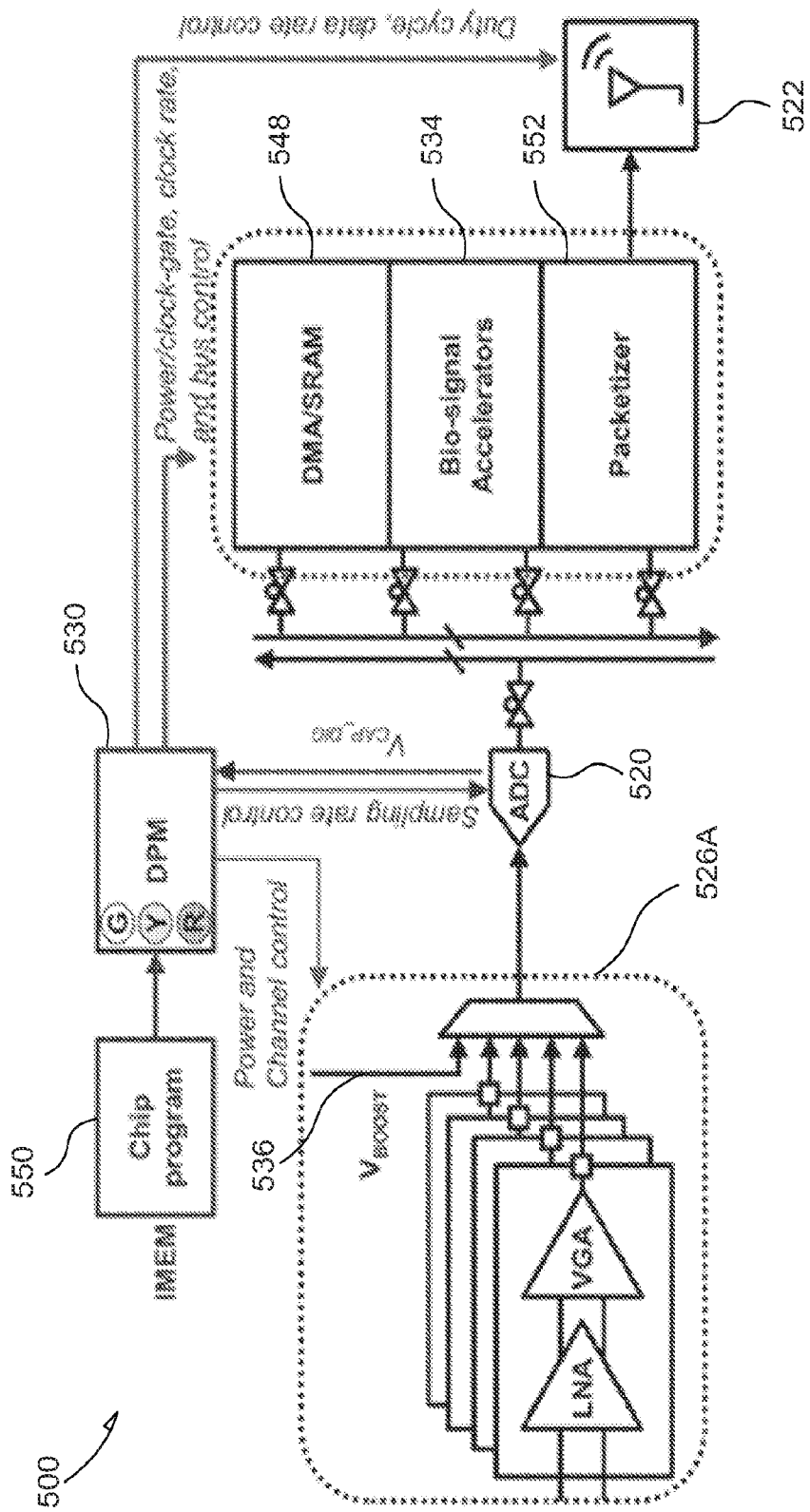
FIG. 5 illustrates generally an illustrative example of a portion of a system that can include an instruction memory coupled to a power management circuit, where the power management circuit can adjust or control various parameters of other functional blocks of the system, such as based on a specified energy consumption level.

FIG. 5 illustrates generally an illustrative example 500 of a portion of a system. The system can include an instruction memory 550 coupled to a power management processor circuit 530 (e.g., DPM), such as where the power management processor circuit 530 can adjust or control various parameters of other functional blocks of the system, such as corresponding to a specified energy consumption level.

In the illustrative example of FIG. 5, the power management processor circuit 530 can monitor an input node to a regulator circuit (e.g., an output of a converter circuit 536), or one or more other nodes. Such monitoring can be performed such as using an analog input 526A similar to the illustrative example of FIG. 9, or as shown one or more other examples. An ADC 520 can provide information indicative of the monitored output of the converter circuit to the power management processor circuit 530. Using this information, the power management processor circuit can automatically adjust an energy consumption level of the system, such as enabling, disabling, or otherwise throttling operation of other functional blocks.

For example, the power management processor circuit 530 can control an energy consumption level of one or more of a memory access controller or data memory circuit 548, one or more or function-specific processor circuits 534, or a wireless transmitter circuit 522. A digital packetizer 552 can be used to stream data to the wireless transmission circuit 522 (e.g., providing serial data for transmission in specified packetized format).

In an example, the system can include direct memory access (DMA) capability, such as allowing one or more portions of the digital section to access the data memory circuit 548. A DMA controller can provide an energy-efficient subthreshold digital circuit to interface between the data memory circuit 548 (DMEM) and one or more other portions of the system. For example, the power management processor circuit can include an instruction to configure the DMA controller to provide access to at least a portion of the DMEM in a FIFO access mode, such as to provide efficient data streaming capability. A clock multiplexer can be used to synchronize a DMA clock rate in correspondence with one or more other functional blocks to which the DMA controller is interfaced. In an example, the data memory circuit 548 can be logically or physically partitioned into banks corresponding to specified energy consumption levels (e.g., using the "stoplight" scheme discussed in one or more illustrative examples herein).

One or more busses, such as two 8-bit switch-box busses, can be controlled by the DPM 530. Such busses can be controllably connected to the inputs or outputs of other portions of the digital section, such as the MCU, DMA, or packetizer 552. In an illustrative example, respective input or output bus ports can have a 4-bit address. Having two or more busses can ease data steering or control.

As discussed in other examples, a system such as a sensor node can include a multi-channel analog input (e.g., AFE), such as the analog input 526A as shown in FIG. 5. For example, the analog input 526A can include four independently configurable input channels, such as including respective fully-differential chopper-stabilized low-noise amplifiers (LNA) or variable-gain amplifiers (VGA). For example, a chopper frequency of about 20 kHz can be used, such as beyond a flicker noise corner of an operational transconductance amplifier (OTA) included in the LNA. Input chopper switches can be placed before input capacitors, such as to reduce any amplification of any OTA offsets that might saturate the OTA output. Mismatch in the input capacitors can result in common-mode to differential-mode gain. Accordingly, for amplification of AC signals, the amplifier can be AC-coupled, such as using an off-chip capacitor and resistor to block or reduce any DC offset voltage at an input.

Such a topology can provide an input impedance that is lower than other corresponding topologies, however it is believed that based on steady-state simulation results, an input impedance can still be on the order of megaOhms (MΩs). Such an input impedance range can be used for physiologic monitoring, such as for monitoring ExG signals or for other sensing applications.

A configurable or programmable Gm-C filter can help to inhibit or reject switching ripple to below a noise floor. In an illustrative example, a coupled LNA and VGA can provide a 7-step digitally-programmable gain (40-78 dB) from DC to 320 Hz at a power consumption of about 3 μW/channel. A 5-input mux, or other topology, as discussed in examples elsewhere herein such as FIG. 9, can provide an input to a sub-μW 8-bit SAR ADC, such as the ADC 520, to sample respective input channels, or the $V_{BOOST}$ converter circuit output node 536, such as for monitoring an energy consumption state or stored energy level.

FIG. 6 illustrates generally an illustrative example 602 of a portion of a system, such as a sensor node, that can include an instruction memory (IMEM) 650 that can be shared between a general-purpose processor circuit (e.g., an MCU 632), a power management processor circuit (e.g., a DPM 630), or one or more other circuits such as a function-specific processor circuit. In the illustrative example 602 of FIG. 6, the MCU can share the IMEM 650 with the DPM 630. For example, respective multiplexers 660A or 660B can steer respective instructions to the MCU 632 or the DPM 630, such as using a specified code word.

In an example, the DPM 630 can be configured to automatically enter a lower energy consumption state (suspended or disabled, such as can be referred as a "sleep" mode), such as when the MCU 632 is executing instructions. Similarly, when the DPM 630 is executing one or more instructions, the MCU 632 can be either turned off, or clock gated to preserve a state, to save energy. In this manner, the MCU 632 can provide general-purpose processing flexibility, and the DPM 630 can provide efficient energy consumption level control, such as without requiring extra instruction or data memory space.

Figure 7:
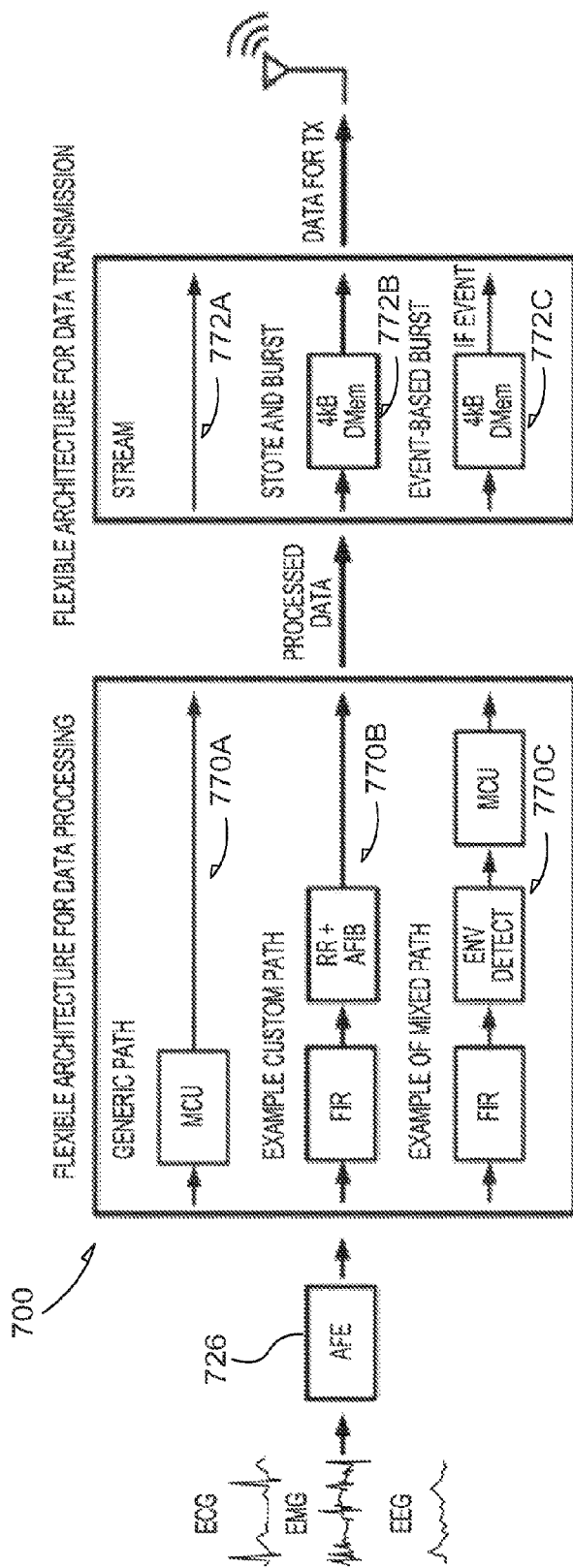
FIG. 7 illustrates generally an illustrative example of a portion of a system that can include one or more controllable data paths for processing of data or for wireless transmission of data, such as can include data paths established based on a specified energy consumption level.

FIG. 7 illustrates generally an illustrative example 700 of a portion of a system, such as a sensor node, that can include one or more controllable data paths for processing of data or for wireless transmission of data, such as can include data paths established corresponding to a specified energy consumption level.

A power management processor circuit, such as the DPM described in examples elsewhere herein, can provide power management responsibility. The DPM can also manage one or more data signal paths, such as in correspondence to a specified energy consumption level. As discussed in illustrative example of FIG. 6, the DPM can execute instructions from an instruction memory (e.g., a 1.5 kB instruction memory), such as consuming less operating energy as compared to using one or more general-purpose processor circuits for controlling the system, as shown in the illustrative example of Table 1, below:

TABLE 1

| DPM instruction | DPM Energy | MCU Equivalent Energy |
| --- | --- | --- |
| NOP | 0.7 pJ | 1.46 pJ |
| Control Signals | 2.8 pJ | 2.92 pJ |
| Branch Commands | 2.9 pJ | 4.38 pJ |

As discussed elsewhere herein, the DPM can include an ISA, such as a simplified ISA as compared to a general-purpose processor circuit. The DPM can be used to control DMEM, input channels of an AFE 726 (e.g., gain or ADC sampling rate, for example), transmission rate, clock frequency creation and distribution, bus management for flexible and timing-defined data flow, time delays, clock-gating, or selection and adjustment of supply voltage provided to various blocks of the system, such as to the digital section of the system. The examples below illustrate generally various examples of signal processing options configurable by the DPM.

FIG. 7 illustrates generally the configurability of the system data path. For example, one or more respective data paths can be established for processing. Similarly, one or more data paths can be established for wireless transmission. As discussed in the examples above and below, a system such as sensor node, can include a general-purpose processor circuit (e.g., MCU). A generic data processing path 770A can be established, such as using the MCU to execute or perform instructions stored in an instruction memory. However, depending on the desired application for the system, other function-specific processor circuits can be used in addition to the MCU or instead of the MCU, such as corresponding to a specified energy consumption level.

A clock generator circuit, such as shown in the example of FIG. 3, can distribute a programmable clock signal (e.g., programmable in one or more of frequency or phase) to respective processor circuits. In this manner, the system can flexibly process data using, for example, one or more of the MCU, one or more function-specific processor circuits, or a cascaded configuration of one or more function specific accelerator circuits and the MCU.

For example, a second data processing path 770B can be selected, such as providing one or more of a finite impulse response (FIR) filter, or an R-wave-to-R-wave interval estimator (e.g., RR extractor), such as coupled to a fibrillation detection circuit. The DPM can automatically select between data processing paths, such as selecting the generic path 770A when plentiful operating energy is established, or selecting the second data processing path 770B in response to monitoring a declining or a lower amount of available operating energy. In an example, a third data processing path 770C can include a combination of function-specific processor circuits, such as one or more of an FIR filter or an envelope detector, such as can be coupled to the MCU.

The general purpose processor circuit, such as the MCU, can include an 8-bit Reduced Instruction Set Computing (RISC) instruction set architecture. One or more digital sections of the system, such as the general-purpose or function-specific processing circuits can include clock gates or headers. For example, PMOS headers can provide a controllable coupling between a respective digital section and one or more regulated supply circuit outputs, such as an 0.5V supply, or an adjustable supply. An adjustable supply can be controlled by the DPM, such as to provide dynamic voltage scaling (DVS).

In an illustrative example, the MCU can be configured to subthreshold operation, such as including an architecture similar to an 8-bit PIC microcontroller (e.g., a PIC microcontroller such as similar to one or more PIC architectures offered by Microchip Technology, Inc., Chandler, Ariz., USA). For example, The MCU can be configured to function down to a VDD voltage of about 0.26V at a clock frequency of about 1.2 kHz. At a VDD voltage of about 0.55V, the MCU can function at about 800 kHz. In an illustrative example, the MCU can consume from about 0.7 nanowatts (nW) to about 1.4 μW, as can be measured corresponding to a supply voltage range from about VDD=0.26 to about VDD=0.55V), such as providing about 1.5 pJ per operation at a default 0.5V, 200 kHz energy consumption level.

The FIR filter can be digital, such as configured to provide a fixed or programmable coefficient set or tap count. In an illustrative example, the FIR filter can include a four-channel programmable architecture, such as permitting up to 30 taps (or more), such as operable in a subthreshold regime down to a supply voltage of about 300 mV (as experimentally determined in this illustrative example). The FIR filter can be configurable, such as including coefficient selection, number of taps, or number of filters. In a specified lower energy consumption mode, the FIR filter can be configured for a "half-tap" operation, such as cutting the number of available taps in half (e.g., transitioning from 30 available taps to 15 available taps).

A direct FIR implementation can include respective multipliers and adders, such as corresponding to respective taps. However, such an approach can cost area and energy consumption performance. For sensing or filtering applications where a sampling rate is relatively low, a serial filter realization can be used, such as determining a given tap multiplication in a serial fashion over time and adding successive determinations, using a clock rate that is a multiple of the sampling rate. Such a serial realization can use as little as a single multiplier and a single adder for respective channels, such as providing a 30× reduction in area as compared to a full 30-tap FIR realization. Such a serial FIR architecture can provide an energy consumption of 1.1 pJ per tap using a supply voltage of 350 mV. Respective channels can be power or clock-gated, such as corresponding to specified energy consumption level as controlled by the DPM.

For physiologic sensing application, such as ExG sensing, one of the function-specific processor circuits can include an envelope detector. For example, for an EEG sensing application, signal power can be determined within specific frequency bands, such as corresponding to neural activity in the α, β, γ, and low-γ frequency bands. An envelope detection circuit can determine the average signal power within a specified frequency band. For example, data can be received from the FIR filter, such as using four input channels corresponding to the channel outputs of the FIR filter. For example, EQN. (1), below, can be used to determine an average signal power, that can be represented by $p_x$ of a signal that can be represented by x, $$p_x = \frac{1}{N} \sum_{n=0}^{N-1} |x[n]|^2 \quad (1)$$

where N can represent the summing window size. To reduce the computation complexity, N can be established as a power of two (e.g., selected from a range of $2^2$ through $2^7$). Such powers of two can provide division operations implemented by right-shifting the data. Values of x can be rounded to the nearest power of 4, such as using squaring results obtained from a look-up table. In this manner the number of bits used during data transformation can be reduced because the least significant two bits are always zero-valued. In an illustrative example, such an envelope detector circuit can be consume 3.5 nW corresponding to a VDD supply voltage of about 0.5V and a clock rate of about 200 kHz.

In an example, the R-R interval estimator can include circuitry to perform a Pan-Tompkins technique. Such an R-R interval estimation technique can include determining heart rate such as using one or more of time windowing and threshold, such as after acquiring a baseline DC value. The R-R interval estimator can provide time stamps given to two consecutive peaks corresponding to the difference in the number of samples between them. In this manner, a resolution of the R-R determination can be adjusted, such as by varying the sampling rate or the supply voltage, such as under the control of the DPM to accommodate a faster or slower processing rate in view of an established energy consumption level.

In an example, once an R-R interval has been estimated, a pulse can be provided, such as to a fibrillation detection processor. For example, the fibrillation detection processor can include an atrial fibrillation detector. The fibrillation detection processor can use one or more fibrillation detection techniques, such as established or verified on a clinical population. The fibrillation detector circuit can output a flag in response to a detected fibrillation event, such as using as few as 12 successive R-R interval estimates along with an entropy threshold criterion, or using one or more other techniques.

The DPM can also control one or more wireless data transmission paths, such as shown in FIG. 7. For example, a first data transmission path 772A can correspond to a streaming mode, such as for transmission of data provided by the MCU. A second transmission path 772B can include a store-and-burst scheme, such as using the data memory circuit (e.g., in a FIFO arrangement). A third transmission path 772C can include storing information, such as in a circular buffer or FIFO, such as transmitting a burst of information in response to one or more detected events. For example, in a physiologic sensing application, information indicative of R-R intervals can be stored. A burst of transmitted information can be provided, such as in response to information indicative of fibrillation. Otherwise, such RR interval information can be stored for later transmission or otherwise discarded.

FIG. 8 illustrates generally an illustrative example 804 of a portion of a system, such as a portion of a regulator circuit that can be included as a portion of a sensor node. As discussed in other examples, an output of an energy harvesting transducer such as a TEG can be boosted. In the example of FIG. 8, an output node 836 of a converter circuit, such as a boost converter, can correspond to a voltage established at a storage capacitor 886. In the illustrative example 804, biases can be generated within an integrated circuit including the regulator circuits of the example 804.

For example, one or more fixed regulators can be included in a fixed-regulator section 884, such as including four or more sub-μW linear regulators. Such regulators can provide specified fixed voltages for coupling to one or more other sections of the system, such as about 1.2V (e.g., coupleable to the AFE), about 0.5V (e.g., for use in digital signal processing, such as one or more function-specific processor circuits or one or more other circuits), about 1.0V (e.g., for supplying a wireless transmitter local oscillator), or another supply configured to generate about 0.5V (e.g., to power a wireless transmitter power amplifier).

The illustrative example of FIG. 8 can include one or more other regulator circuits, such as an adjustable regulator section 882. For example, the adjustable regulator section 882 can include a switched-capacitor DC-DC converter. The converter can be configured to provide an adjustable or controllable output form about 0.25V to 1V, such as in 50 mV steps. For example, a 3-bit resistor DAC (RDAC) can be used to generate a reference voltage corresponding to a desired output level, such as based on a control word from the DPM. The arrangement of the capacitors in the array can be varied such as according to the desired output range. One or more external capacitors can be coupled to the adjustable regulator section 882, such as to reduce or inhibit ripple due to switching activity.

As discussed in other examples herein, one or more of sections of the system can be configured for subthreshold operation, such as controllably coupleable to a fixed or a variable voltage supply, such as using PMOS headers, such as under the control of the DPM. In this manner, the DPM can establish a controlled energy consumption level for each section, using one or more of the fixed or adjustable supply voltages.

FIG. 9 illustrates generally an illustrative example 900 of a portion of a system, such as a sensor node. The illustrative example 900 can include a monitoring circuit configured to provide information indicative of a regulator circuit input. The system can monitor an energy consumption level of the system. Such monitored information can be used adjust a mode of operation accordingly, such as to prevent a system reset or system extinction. For example, if monitored information indicative of the regulator input node (e.g., a boost converter circuit output node 986, $V_{BOOST}$) is decreasing, the system can switch modes and consume less energy to sustain operation. When harvested energy becomes abundant, the system can recover or adjust itself to a mode providing full or unrestricted operation, or maintain operation in such a mode.

The DPM 930 (e.g., a digital power management processor circuit) can be configured to monitor the boost converter output node 986 (e.g., $V_{BOOST}$), or one or more other nodes, such as to provide closed-loop energy consumption management in some or all operable modes of the system. The DPM 930 can provide energy data flow management or other supervisory functions, such as corresponding to a specified energy consumption level that may be determined at least in part using monitored information obtained using a circuit as shown in the illustrative example of FIG. 9.

For example, the DPM 930 can monitor a representation of $V_{BOOST}$ through an ADC 920. The representation of the $V_{BOOST}$ provided to the ADC 920 can be scaled to take advantage of at or near the ADC's full input range. For example, $V_{BOOST}$ can be halved by a resistive divider, buffered to reduce output impedance using a buffer circuit 990, or compared with a reference voltage using a difference amplifier circuit 992. For example, the difference between $V_{BOOST}$ and the reference voltage can be amplified by four times such as through the difference amplifier circuit 992, such as including one or more OTAs. Periodically, or during specified durations, the DPM can issue an instruction to select an input channel of a multiplexer 926A, such as amongst other channels (e.g., other channels 1 through 4 such as can be provided by the AFE), to obtain information indicative of the energy consumption level of the system.

The scaled or digitized representation of the $V_{BOOST}$ voltage, which can be represented by $V_{CAP\_DIG}$, can be provided to the DPM 930, such as in response to the issued instruction. In response to this monitored information, the DPM 930 can adjust or select an energy consumption level of the system, such as using a stoplight scheme.

Figure 10:
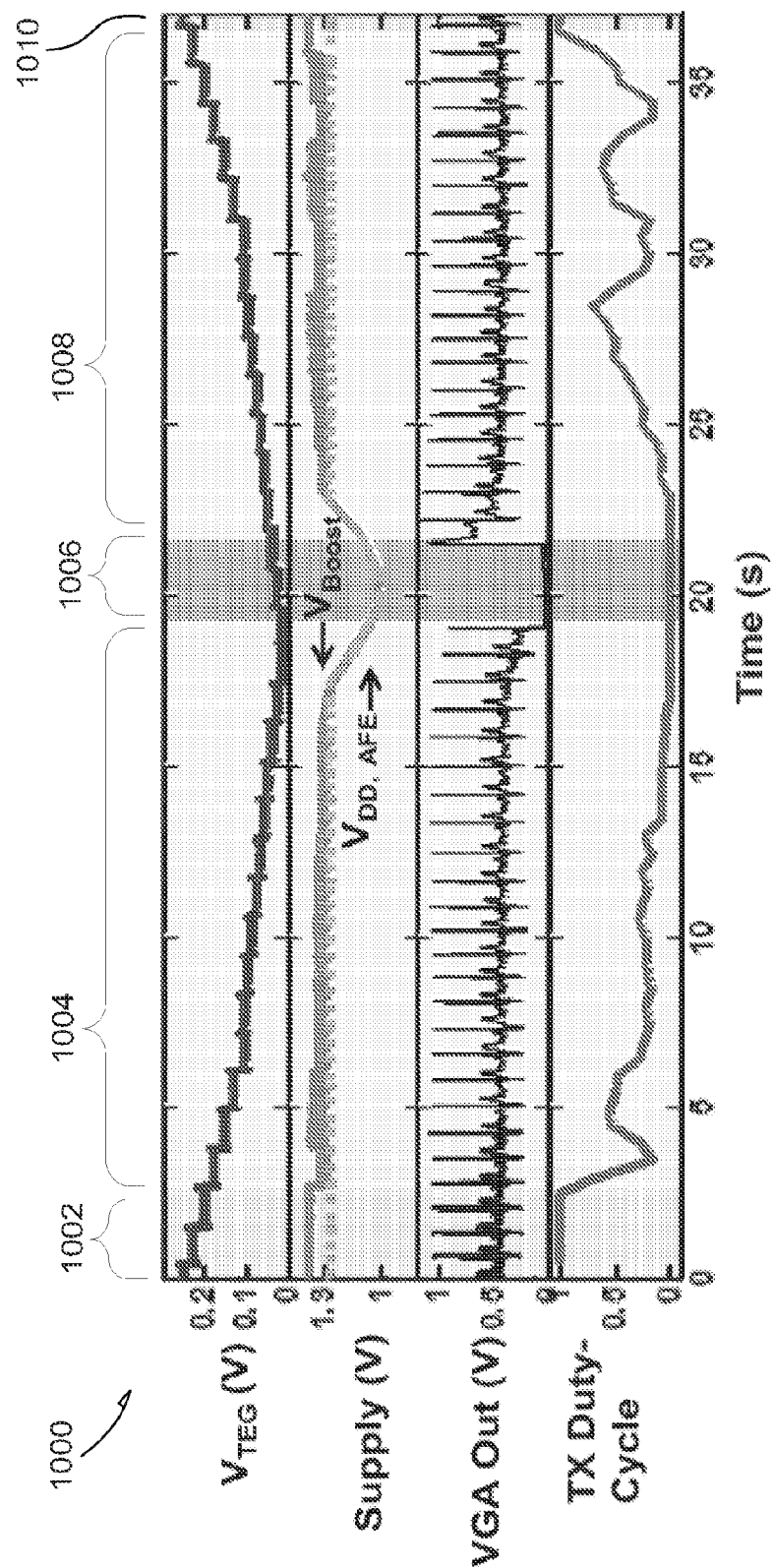
FIG. 10 illustrates generally an illustrative example of plots including various parameters of a system obtained in correspondence with different automatically-controlled energy consumption levels, such as can be obtained experimentally using a system as shown in the example of FIG. 3.

FIG. 10 illustrates generally an illustrative example 1000 of plots corresponding to various parameters of a system corresponding to different automatically-controlled energy consumption levels, such as can be obtained experimentally using a system as shown in the example of FIG. 3, or as discussed above in relation to the illustrative example of FIG. 9. Such a scheme can be used to automatically select or adjust an energy consumption level of the system, such as using one or more fixed or programmable thresholds or windows.

In an illustrative example, the DPM 930 can compare the obtained information (e.g., $V_{CAP\_DIG}$) to one or more programmable threshold values, such as can include two 8-bit threshold values (e.g., a green threshold, a yellow threshold), such as to select an energy consumption level (e.g., a green level or mode, a yellow level or mode, a red level or mode). The DPM 930 can be configured to jump from a present energy consumption level to any other levels, such as without requiring a sequential transition through any intermediate level (e.g., a transition can include a green-to-red mode switch, etc.).

Respective energy consumption levels (e.g., operating modes) can correspond to a respective subset or superset of blocks that can be configured to provide respective energy consumption levels. An illustrative example of such control can be found in Table 2:

TABLE 2

| Energy Consumption Level | Inst. Mem. | AFE | Data Mem. | Function-Specific Circuits | Wireless Transmitter |
|---|---|---|---|---|---|
| Red | On | Off | Off | Off | Off |
| Yellow | On | On | On | On | Off or Duty Cycled |
| Green | On | On | On | On | On |

In the illustrative example of FIG. 10, an input to the boost converter can be swept through a range from about 250 mV to 20 mV and back. For example, operation in the green mode (e.g., VBOOST greater than about 1.3V) can allow most or all functional blocks of the system to be operational, such as shown in the first green region 1002 of FIG. 10, or the second green region 1010.

In the yellow mode (e.g., $V_{BOOST}$ greater than about 1.1V and less than about 1.3V), the DPM can switch off or duty cycle the transmitter based on available energy, such as shown in the first yellow region 1004, or the second yellow region 1008 of FIG. 10.

In the red mode (e.g., $V_{BOOST}$ less than about 1.1V), the transmitter, function-specific processor circuits, or the AFE can be one or more of clock or power-gated to conserve energy, such as shown in the red region 1006 of FIG. 10.

The DPM can override or otherwise alter system execution. For example, even if the system calls for operation of one or more disabled or throttled blocks for a particular series of operations, the DPM can override such calls in accordance with the energy consumption level established by the "stoplight" scheme. The DPM can transition contemporaneously from mode to mode, such as in response to monitored information such as an 8-bit digital $V_{CAP\_DIG}$ determination, such as without requiring additional instructions. In such a manner, a closed-loop energy consumption management scheme can be provided. The "stoplight" scheme can be used to provide branching or jumping behavior in the DPM or a general-purpose processor circuit, such as to alter node behavior during or after an energy consumption level change.

The energy consumption management scheme shown and described in the examples of FIGS. 9 and 10 can be flexible, such as using adjustable or user-programmable threshold values or parameters to control a duration between energy consumption sampling operations.

In an example, the energy consumption level established by the DPM can be overridden by one or more other system elements, such as to monitor or transmit information deemed important enough to risk a sensor node reset or extinction. Such override capability can occur in response to a specified event or flag, such as provided by one or more of the function-specific processor circuits.

Figure 11A:
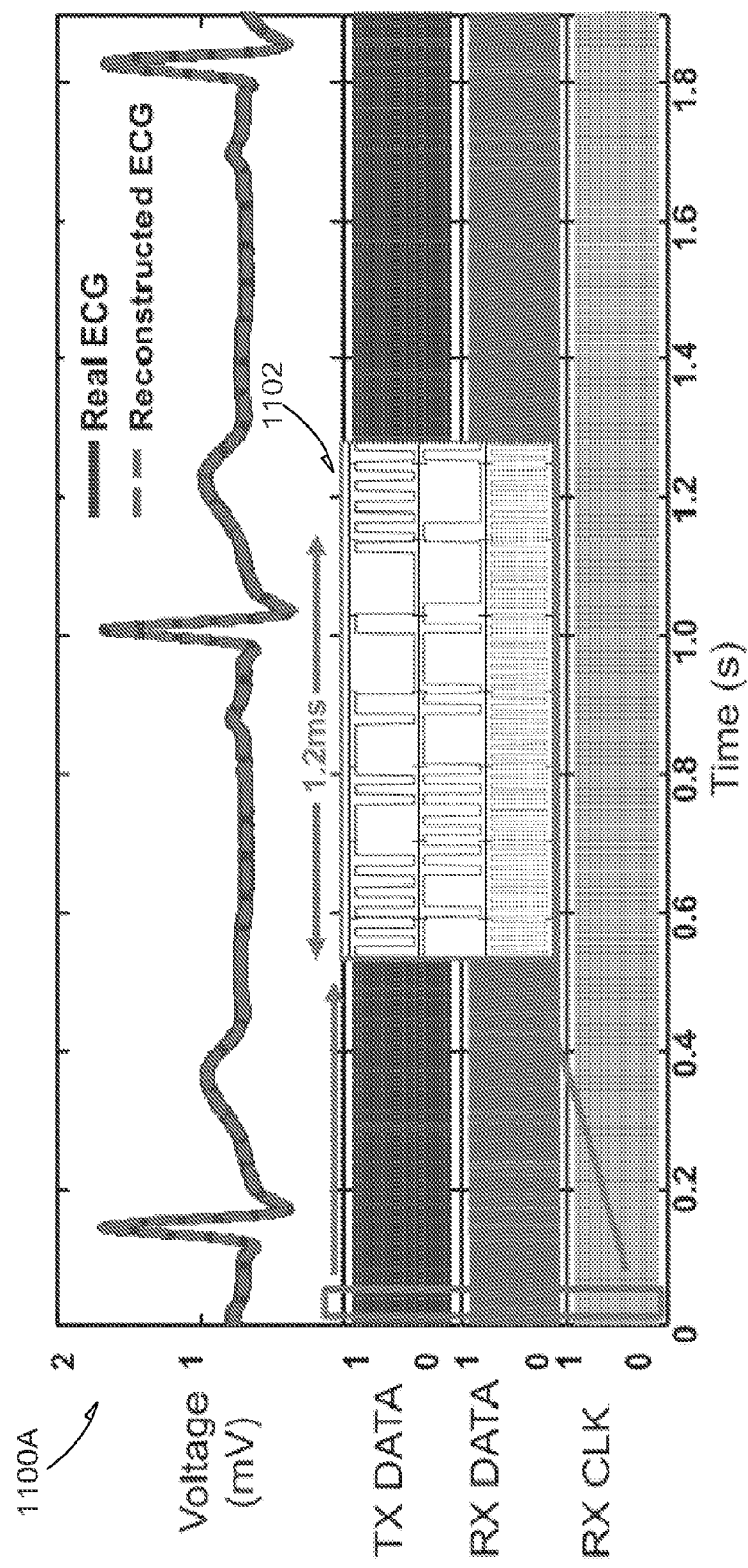
FIG. 11A illustrates generally an illustrative example of plots corresponding to an actual and a reconstructed representation of an electrocardiogram such as can be transmitted in real-time or near-real time by a system, such as a sensor node.

FIG. 11A illustrates generally an illustrative example 1100A of plots corresponding to an actual and a reconstructed representation of an electrocardiogram such as can be transmitted in real-time or near-real time by a system, such as a sensor node. In the illustrative example of FIG. 11A, an ECG was obtained from a healthy human subject, and transmitted by the wireless communication circuit in a raw streaming mode, such as consuming 397 μW as measured from the 1.35V $V_{BOOST}$ node). The wireless transmitted information was received by a Texas Instruments CC1101, using a frequency of about 433 MHz. The received reconstructed ECG (dashed) generally corresponds to the actual locally-measured ECG.

Figure 11B:
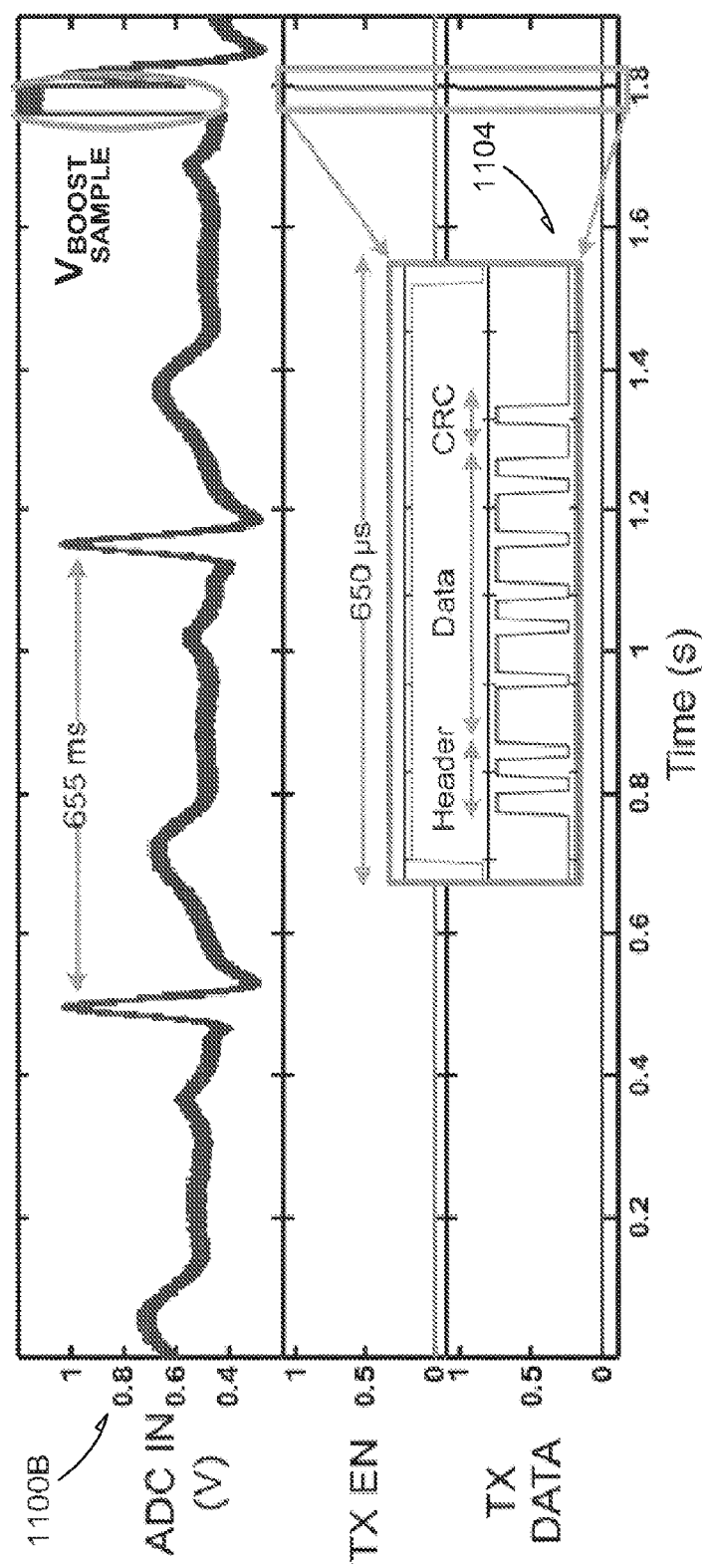
FIG. 11B illustrates generally an illustrative example of plots corresponding to a sensed representation of information provided to an analog-to-digital converter input, including a duration where the input can be switched to sample an input to a regulator circuit, such as for monitoring the input to the regulator circuit.

FIG. 11B illustrates generally an illustrative example 1100B of plots corresponding to a sensed representation of information provided to an analog-to-digital converter input, including a duration where the input can be switched to sample a $V_{BOOST}$ node (e.g., an output node of a boost converter circuit). In the illustrative example of FIG. 11B, the system can operate using an R-R interval extraction technique, such as transmitting a measured hear rate at periodic or specific intervals, such as every 5 seconds when operating from an energy harvesting input of about 30 mV. During successive intervals, $V_{BOOST}$ can also be sampled, such as to verify that sufficient energy exists to sustain continued operation, such as before enabling a crystal oscillator for wireless transmission of information.

FIG. 12B illustrates generally an annotated micrograph 1200 of an integrated circuit, such as corresponding to at least a portion of the system of the illustrative examples of FIG. 1-3, 4A, 5-10, or 12. Such an integrated circuit can include an SoC for operation of a sensor node or other embedded system. In an illustrative example, such as corresponding to a heart-rate extraction mode, where the wireless transmitter circuit can be duty-cycle, the SoC can consume about 19 μW, which is believed to be less than other generally-available systems.

Figure 13:
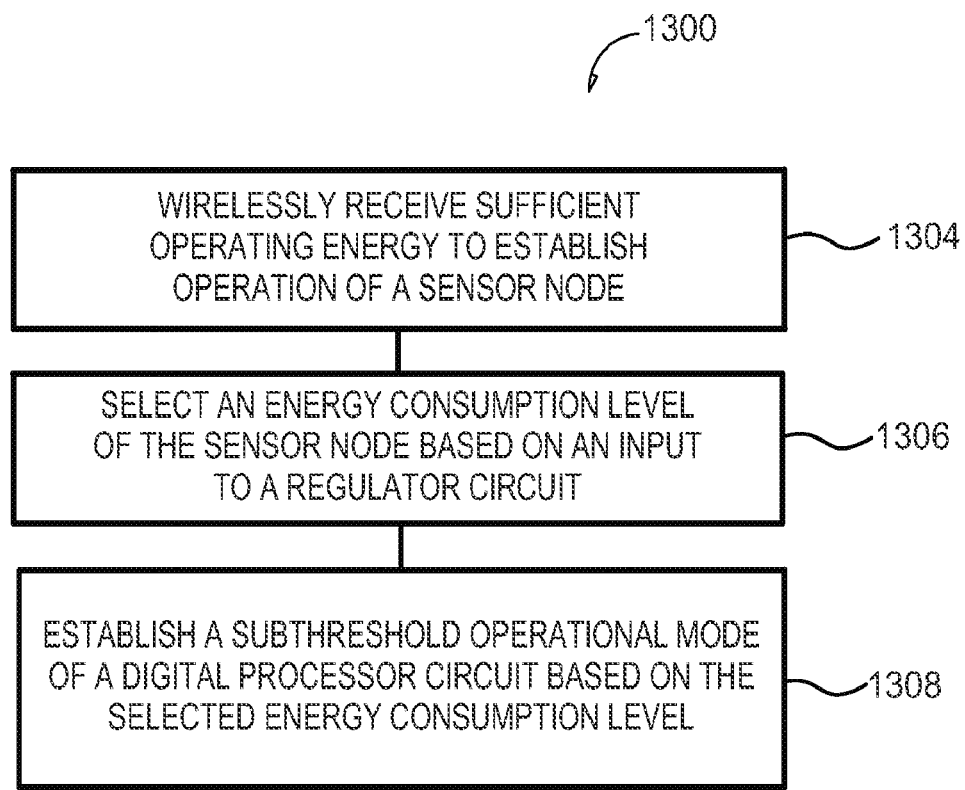
FIG. 13 illustrates generally a technique, such as a method, that can include using a system as shown in the examples of one or more of FIGS. 1 through 9.

FIG. 13 illustrates generally a technique 1300, such as a method, that can include using a system as shown in the examples of one or more of FIG. 1-3, 4A, 5-10, or 12. A wireless receiver circuit can be coupled to a regulator circuit, such as shown in the example of FIG. 1. The wireless receiver circuit can be configured to obtain electromagnetically-coupled operating energy, such as to establish initial operation or provide continued operation of a system such as sensor node, such as at 1304. For example, the sensor node can wireless receive sufficient operating energy to establish operation of the sensor node without requiring operating energy obtained from an energy harvesting transducer, even though such a transducer may be coupled to the regulator circuit.

An input to a regulator circuit can be monitored, such as for use in selecting an energy consumption level of a sensor node. For example, at 1306, the energy consumption level of the sensor node can be selected based on an input to the regulator circuit. At 1308, a subthreshold operational mode can be established in one or more portions of the system, such as in relation to operation of a digital processor circuit. The subthreshold operation mode can correspond to a selected energy consumption level of the system.

VARIOUS NOTES & EXAMPLES

Each of the non-limiting examples described in this document can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A sensor node, comprising:
a regulator circuit including an input coupleable to an energy harvesting transducer;
a wireless receiver circuit coupled to the regulator circuit and configured to wirelessly receive at least enough operating energy to establish operation of the sensor node without requiring the energy harvesting transducer;
a digital processor circuit coupled to the regulator circuit; and
a power management processor circuit configured to select an energy consumption level of the sensor node based on an input to the regulator circuit;
wherein the digital processor circuit includes a subthreshold operational mode established by the power management processor circuit based on the selected energy consumption level; and
wherein establishing the subthreshold operational mode includes adjusting or selecting a supply voltage provided by the regulator circuit so as to establish subthreshold operation of a field effect transistor (FET) in the digital processor circuit.

2. The sensor node of claim 1, further comprising the energy harvesting transducer coupled to the regulator circuit;
wherein the regulator circuit is configured to provide sufficient operating energy for the sensor node to operate continuously when coupled to the energy harvesting transducer and without requiring a primary or rechargeable battery.

3. The sensor node of claim 2, wherein the wireless receiver circuit is configured to wirelessly receive at least enough operating energy to establish operation of the sensor node initially; and
wherein the regulator circuit and energy harvesting transducer are configured to provide sustained operating energy for the sensor node in the absence of further wirelessly-received operating energy.

4. The sensor node of claim 2, wherein the energy harvesting transducer includes a thermoelectric generator (TEG).

5. The sensor node of claim 1, wherein the power management processor circuit is configured to select the energy consumption level of the sensor node at least in part to inhibit a reset or to inhibit an extinction of operation of the sensor node.

6. The sensor node of claim 1, comprising a function-specific processor circuit including a subthreshold operational mode established by the power management processor circuit based on the selected energy consumption level;
wherein the digital processor circuit comprises a general-purpose processor circuit;
wherein the regulator circuit includes an adjustable output configured to provide the supply voltage to the general-purpose processor circuit and/or the function-specific processor circuit; and
wherein establishing the subthreshold operational mode includes adjusting the adjustable output so as to establish subthreshold operation of a respective field effect transistor (FET) in the general-purpose processor circuit and/or the function-specific processor circuit.

7. The sensor node of claim 1, comprising a function-specific processor circuit including a subthreshold operational mode established by the power management processor circuit based on the selected energy consumption level;
wherein the digital processor circuit comprises a general-purpose processor circuit;
wherein the regulator circuit includes two or more outputs configured to provide different specified supply voltages controllably coupleable to the general-purpose processor circuit and/or the function-specific processor circuit; and
wherein the power management circuit is configured to control coupling of the respective outputs of the regulator circuit to the general-purpose processor circuit and/or the function-specific processor circuit to establish the subthreshold operational mode.

8. The sensor node of claim 1, comprising a clock generation circuit configured to provide a specified output clock frequency at a clock output;
wherein the power management processor circuit is configured to adjust the output clock frequency provided to the digital processor circuit, or to gate the clock output provided to the digital processor circuit, based on the selected energy consumption level.

9. The sensor node of claim 1, comprising:
an analog input configured to obtain information indicative of a physiologic signal, the analog input controllably coupleable to the digital processor circuit under the control of the power management circuit and based on the selected energy consumption level.

10. The sensor node of claim 9, wherein the analog input includes an analog-to-digital converter;
wherein the power management circuit is configured to obtain information indicative of the input to the regulator circuit using the analog-to-digital converter; and
wherein the power management circuit is configured to adjust the energy consumption level of the sensor node using the obtained information about the input to the regulator circuit.

11. The sensor node of claim 9, comprising a wireless transmitter controllably coupleable to the digital processor circuit or to the analog input, the wireless transmitter configured to transmit one or more of streamed or processed information indicative of the physiologic signal obtained by the analog input under the control of the power management circuit and based on the selected energy consumption level.

12. The sensor node of claim 11, comprising a function-specific processor circuit including a subthreshold operational mode established by the power management processor circuit based on the selected energy consumption level;
wherein the digital processor circuit comprises a general-purpose processor circuit; and
wherein the power management circuit is configured to controllably establish a data path between the analog input and the wireless transmitter to include or exclude the general-purpose processor circuit and/or the function-specific processor circuit based on the selected energy consumption level.

13. The sensor node of claim 11, comprising a function-specific processor circuit, wherein the energy consumption level includes at least three levels, including:
a first energy consumption level wherein a general-purpose processor circuit, the function-specific processor circuit, the analog input, and the wireless transmitter are enabled;

a second energy consumption level wherein the wireless transmitter is duty-cycled to consume less energy than the corresponding energy consumption of the wireless transmitter when the first energy consumption level is selected; and a third energy consumption level wherein:
the wireless transmitter is further duty-cycled or disabled to consume less energy than the corresponding energy consumption of the wireless transmitter when the first or second energy consumption levels are selected, and
wherein the general-purpose processor circuit, the function-specific processor circuit, and/or the analog input are inhibited from receiving one or more of a clock signal or a supply voltage.

14. The sensor node of claim 1, comprising a commonly-shared instruction memory circuit coupled to the power management circuit and the digital processor circuit.

15. The sensor node of claim 14, comprising a data memory circuit coupled to one or more of the power management circuit and the digital processor circuit.

16. The sensor node of claim 1, wherein active portions of the regulator circuit, the wireless receiver circuit, the digital processor circuit, and the power management circuit are co-integrated in a commonly-shared integrated circuit device.

17. The sensor node of claim 16, wherein the integrated circuit device comprises a complementary metal-oxide-semiconductor (CMOS) device.

18. The sensor node of claim 1, wherein the wireless receiver circuit is configured to receive one or more of inductively-coupled electromagnetic operating energy or radiatively-coupled electromagnetic operating energy.

19. A method of operating a sensor node, comprising:
wirelessly receiving, at a wireless receiver circuit coupled to a regulator circuit coupleable to an energy harvesting transducer, sufficient operating energy to establish operation of a sensor node without requiring operating energy from the energy harvesting transducer;
selecting an energy consumption level of the sensor node based on an input to the regulator circuit; and
establishing a subthreshold operational mode of a digital processor circuit based on the selected energy consumption level, including adjusting or selecting a supply voltage provided by the regulator circuit so as to establish subthreshold operation of a field effect transistor (FET) in the digital processor circuit.

20. The method of claim 19, comprising obtaining sufficient operating energy for the sensor node to operate continuously using the energy harvesting transducer without requiring a primary or rechargeable battery.

21. The method of claim 20, comprising:
wirelessly receiving, at a wireless receiver circuit enough operating energy to establish operation of the sensor node initially; and
obtaining sustained operating energy for operation of the sensor node using the energy harvesting transducer in the absence of further wirelessly-received operating energy.

22. The method of claim 20, wherein the energy harvesting transducer includes a thermoelectric generator (TEG).

23. The method of claim 19, comprising selecting the energy consumption level of the sensor node at least in part to inhibit a reset or to inhibit an extinction of operation of the sensor node.

24. The method of claim 19, comprising adjusting an output of the regulator circuit to provide a supply voltage to a general-purpose processor circuit and/or a function-specific processor circuit;
wherein establishing the subthreshold operational mode includes adjusting the adjustable output so as to establish subthreshold operation of a respective field effect transistor (FET) in the general-purpose processor circuit and/or the function-specific processor circuit.

25. The method of claim 19, comprising controllably coupling respective different outputs of the regulator circuit to a general-purpose processor circuit and/or a function-specific processor circuit to establish the subthreshold operational mode.

26. The method of claim 19, comprising generating a specified output clock frequency at a clock output, including adjusting the output clock frequency provided to the digital processor circuit, or gating the clock output provided to the digital processor circuit, based on the selected energy consumption level.

27. The method of claim 19, comprising obtaining information indicative of a physiologic signal using an analog input controllably coupleable to the digital processor circuit based on the selected energy consumption level.

28. The method of claim 27, wherein the physiologic signal includes one or more of an electrocardiogram (ECG), and electroencephalogram (EEG), or an electromyogram (EMG).

29. The method of claim 27, comprising adjusting the energy consumption level of the sensor node using obtained information about the input to the regulator circuit, the information obtained using the analog input.

30. The method of claim 27, comprising wirelessly transmitting one or more of streamed or processed information indicative of the physiologic signal obtained by the analog input based on the selected energy consumption level, using a wireless transmitter.

31. The method of claim 29, comprising controllably establishing a data path between the analog input and a wireless transmitter to include or exclude a general-purpose processor circuit and/or a function-specific accelerator circuit based on the selected energy consumption level.

32. The method of claim 29, wherein the energy consumption level includes at least three levels, including:
a first energy consumption level wherein the general-purpose processor circuit, a function-specific processor circuit, the analog input, and the wireless transmitter are enabled;
a second energy consumption level wherein the wireless transmitter is duty-cycled to consume less energy than the corresponding energy consumption of the wireless transmitter when the first energy consumption level is selected; and
a third energy consumption level wherein:
the wireless transmitter is further duty-cycled or disabled to consume less energy than the corresponding energy consumption of the wireless transmitter when the first or second energy consumption levels are selected, and
wherein the general-purpose processor circuit, the function-specific processor circuit, and/or the analog input are inhibited from receiving one or more of a clock signal or a supply voltage.

33. A processor-readable medium including instructions that, when executed by at least one processor circuit, cause an apparatus including the at least one processor circuit to perform a method comprising the steps of:

wirelessly receiving, at a wireless receiver circuit coupled to a regulator circuit coupleable to an energy harvesting transducer, sufficient operating energy to establish operation of a sensor node without requiring operating energy from the energy harvesting transducer;

selecting an energy consumption level of the sensor node based on an input to the regulator circuit; and establishing a subthreshold operational mode of a digital processor circuit based on the selected energy consumption level, including adjusting or selecting a supply voltage provided by the regulator circuit so as to establish subthreshold operation of a field effect transistor (FET) in the digital processor circuit.

* * * * *